US012156938B2

(12) United States Patent
Prakash et al.

(10) Patent No.: US 12,156,938 B2
(45) Date of Patent: Dec. 3, 2024

(54) LIPOSOMES FOR TARGETING TUMOR-ASSOCIATED MACROPHAGES

(71) Applicant: Universiteit Twente, Enschede (NL)

(72) Inventors: Jai Prakash, Enschede (NL); Peter Van Hoogevest, Neustadt an der Weinstraße (DE); Gerrit Storm, Utrecht (NL)

(73) Assignee: Universiteit Twente, Enschede (NL)

( * ) Notice: Subject to any disclaimer, the term of this patent is extended or adjusted under 35 U.S.C. 154(b) by 928 days.

(21) Appl. No.: 16/982,990

(22) PCT Filed: Mar. 20, 2019

(86) PCT No.: PCT/NL2019/050170

§ 371 (c)(1),
(2) Date: Sep. 21, 2020

(87) PCT Pub. No.: WO2019/182441

PCT Pub. Date: Sep. 26, 2019

(65) Prior Publication Data

US 2023/0165795 A1 Jun. 1, 2023

(30) Foreign Application Priority Data

Mar. 20, 2018 (EP) .................................... 18162956

(51) Int. Cl.

| | |
|---|---|
| ***A61K 9/127*** | (2006.01) |
| ***A61K 38/05*** | (2006.01) |
| ***A61K 38/21*** | (2006.01) |
| ***A61K 47/40*** | (2006.01) |

(52) U.S. Cl.

CPC .............. *A61K 9/127* (2013.01); *A61K 38/05* (2013.01); *A61K 38/217* (2013.01); *A61K 47/40* (2013.01)

(58) Field of Classification Search

None

See application file for complete search history.

(56) References Cited

U.S. PATENT DOCUMENTS

| | | | | |
|---|---|---|---|---|
| 2014/0161733 A1* | 6/2014 | Zhou | .................. | A61K 49/1812 424/9.323 |
| 2014/0271820 A1 | 9/2014 | McGhee | | |
| 2014/0287024 A1* | 9/2014 | Wang | ................. | A61K 39/3955 514/456 |

FOREIGN PATENT DOCUMENTS

| | | | |
|---|---|---|---|
| WO | 97/04747 | * | 2/1997 |

OTHER PUBLICATIONS

International Search Report for International Application No. PCT/NL2019/050170, mailed Jun. 14, 2019, 4 pages.

International Written Opinion for International Application No. PCT/NL2019/050170, mailed Jun. 14, 2019, 6 pages.

Runas et al, "Low levels of lipid oxidation radically increase the passive permeability of lipid bilayers", Soft Matter, vol. 11, No. 3, Jan. 1, 2015 (Jan. 1, 2015), p. 499-505, XP055502338, DOI: 10.1039/C4SM01478B.

Kuninty et al. "Cancer immune therapy using engineered 'tail-flipping' nanoliposomes targeting alternatively activated macrophages" Nature Communications 13:4548 (Published online Aug. 4, 2022) https://doi.org/10.1038/s41467-022-32091-9.

Kunnity et al. "Cancer immune therapy using engineered 'tail-flipping' nanoliposomes targeting alternatively activated macrophages" Nature Communications13:45-48 (published online: Aug. 4, 2022).

* cited by examiner

*Primary Examiner* — Nannette Holloman

(74) *Attorney, Agent, or Firm* — TraskBritt

(57) ABSTRACT

A composition comprising a liposome comprising a first phospholipid comprising a $C_{14}$-$C_{19}$:0 fatty acid and a $C_3$-$C_{15}$:0 fatty acid with a c-terminal carboxyl or a carboxaldehyde group; a second phospholipid comprising a $C_{14}$-$C_{19}$:0 fatty acid and a $C_{14}$-$C_{19}$:0 fatty acid and a sterol. The first phospholipid is preferably a phosphatidylcholine. The second phospholipid is preferably HSPC and the sterol is preferably cholesterol. In some embodiments, the molar ratio of the respective ingredients is 2-3:5-6:2-3; preferably 2:6:2; or 3:5:2, respectively. The invention also relates to the use of this composition in the targeting of M2 macrophages.

9 Claims, 8 Drawing Sheets

Specification includes a Sequence Listing.

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Arg-1 (m) FW

<400> SEQUENCE: 1

gtgaagaacc cacggtctgt                                                20


<210> SEQ ID NO 2
<211> LENGTH: 20
```

-continued

<212> TYPE: DNA
<213> ORGANISM: Artificial Sequence
<220> FEATURE:
<223> OTHER INFORMATION: Arg-1 (m) RV

<400> SEQUENCE: 2
ctggttgtca ggggagtgtt 20

<210> SEQ ID NO 3
<211> LENGTH: 20
<212> TYPE: DNA
<213> ORGANISM: Artificial Sequence
<220> FEATURE:
<223> OTHER INFORMATION: Cd36 (h) FW

<400> SEQUENCE: 3
tggcaacaaa ccacacactg 20

<210> SEQ ID NO 4
<211> LENGTH: 21
<212> TYPE: DNA
<213> ORGANISM: Artificial Sequence
<220> FEATURE:
<223> OTHER INFORMATION: Cd36 (h) RV

<400> SEQUENCE: 4
aagtcctaca ctgcagtcct c 21

<210> SEQ ID NO 5
<211> LENGTH: 22
<212> TYPE: DNA
<213> ORGANISM: Artificial Sequence
<220> FEATURE:
<223> OTHER INFORMATION: Colec12 (h) FW

<400> SEQUENCE: 5
aggtcgaggt tagacactga ag 22

<210> SEQ ID NO 6
<211> LENGTH: 22
<212> TYPE: DNA
<213> ORGANISM: Artificial Sequence
<220> FEATURE:
<223> OTHER INFORMATION: Colec12 (h) RV

<400> SEQUENCE: 6
gatcctctgt cacctcttgg ac 22

<210> SEQ ID NO 7
<211> LENGTH: 20
<212> TYPE: DNA
<213> ORGANISM: Artificial Sequence
<220> FEATURE:
<223> OTHER INFORMATION: Dc-sign (h) FW

<400> SEQUENCE: 7
gaactggcac gactccatca 20

<210> SEQ ID NO 8
<211> LENGTH: 20
<212> TYPE: DNA
<213> ORGANISM: Artificial Sequence
<220> FEATURE:
<223> OTHER INFORMATION: Dc-sign (h) RV

<400> SEQUENCE: 8

-continued ctggaagact gctcctcagc 20

<210> SEQ ID NO 9
<211> LENGTH: 20
<212> TYPE: DNA
<213> ORGANISM: Artificial Sequence
<220> FEATURE:
<223> OTHER INFORMATION: Dectin-1 (h) FW

<400> SEQUENCE: 9
atggctctgg gaggatggat 20

<210> SEQ ID NO 10
<211> LENGTH: 20
<212> TYPE: DNA
<213> ORGANISM: Artificial Sequence
<220> FEATURE:
<223> OTHER INFORMATION: Dectin-1 (h) RV

<400> SEQUENCE: 10
gggcacacta cacagttggt 20

<210> SEQ ID NO 11
<211> LENGTH: 20
<212> TYPE: DNA
<213> ORGANISM: Artificial Sequence
<220> FEATURE:
<223> OTHER INFORMATION: Gapdh (m) FW

<400> SEQUENCE: 11
acagtccatg ccatcactgc 20

<210> SEQ ID NO 12
<211> LENGTH: 20
<212> TYPE: DNA
<213> ORGANISM: Artificial Sequence
<220> FEATURE:
<223> OTHER INFORMATION: Gapdh (m) RV

<400> SEQUENCE: 12
gatccacgac ggacacattg 20

<210> SEQ ID NO 13
<211> LENGTH: 20
<212> TYPE: DNA
<213> ORGANISM: Artificial Sequence
<220> FEATURE:
<223> OTHER INFORMATION: Il-1b (h) FW

<400> SEQUENCE: 13
cagaagtacc tgagctcgcc 20

<210> SEQ ID NO 14
<211> LENGTH: 20
<212> TYPE: DNA
<213> ORGANISM: Artificial Sequence
<220> FEATURE:
<223> OTHER INFORMATION: IL-1b (h) RV

<400> SEQUENCE: 14
agattcgtag ctggatgccg 20

<210> SEQ ID NO 15
<211> LENGTH: 20
<212> TYPE: DNA
<213> ORGANISM: Artificial Sequence
<220> FEATURE:
<223> OTHER INFORMATION: Il-6 (h) FW

<400> SEQUENCE: 15
tgcaataacc acccctgacc 20

<210> SEQ ID NO 16
<211> LENGTH: 20
<212> TYPE: DNA
<213> ORGANISM: Artificial Sequence
<220> FEATURE:
<223> OTHER INFORMATION: Il-6 (h) RV

<400> SEQUENCE: 16
atttgccgaa gagccctcag 20

<210> SEQ ID NO 17
<211> LENGTH: 22
<212> TYPE: DNA
<213> ORGANISM: Artificial Sequence
<220> FEATURE:
<223> OTHER INFORMATION: Il-6 (m) FW

<400> SEQUENCE: 17
tgatgctggt gacaaccacg gc 22

<210> SEQ ID NO 18
<211> LENGTH: 25
<212> TYPE: DNA
<213> ORGANISM: Artificial Sequence
<220> FEATURE:
<223> OTHER INFORMATION: Il-6 (m) RV

<400> SEQUENCE: 18
taagcctccg acttgtgaag tggta 25

<210> SEQ ID NO 19
<211> LENGTH: 20
<212> TYPE: DNA
<213> ORGANISM: Artificial Sequence
<220> FEATURE:
<223> OTHER INFORMATION: Rps18 (h) FW

<400> SEQUENCE: 19
tgaggtggaa cgtgtgatca 20

<210> SEQ ID NO 20
<211> LENGTH: 20
<212> TYPE: DNA
<213> ORGANISM: Artificial Sequence
<220> FEATURE:
<223> OTHER INFORMATION: Rps18 (h) RV

<400> SEQUENCE: 20
cctctatggg cccgaatctt 20

<210> SEQ ID NO 21
<211> LENGTH: 21
<212> TYPE: DNA
<213> ORGANISM: Artificial Sequence
<220> FEATURE:
<223> OTHER INFORMATION: Scarb1 (h)

<400> SEQUENCE: 21
aagattgagc ctgtggtcct g 21

-continued

```
<210> SEQ ID NO 22
<211> LENGTH: 21
<212> TYPE: DNA
<213> ORGANISM: Artificial Sequence
<220> FEATURE:
<223> OTHER INFORMATION: Scarb1 (h) RV

<400> SEQUENCE: 22

cctccttatc ctttgagccc t                                    21


<210> SEQ ID NO 23
<211> LENGTH: 20
<212> TYPE: DNA
<213> ORGANISM: Artificial Sequence
<220> FEATURE:
<223> OTHER INFORMATION: Tnf-a (h) FW

<400> SEQUENCE: 23

cttctgcctg ctgcactttg                                      20


<210> SEQ ID NO 24
<211> LENGTH: 20
<212> TYPE: DNA
<213> ORGANISM: Artificial Sequence
<220> FEATURE:
<223> OTHER INFORMATION: Tnf-a (h) RV

<400> SEQUENCE: 24

gtcactcggg gttcgagaag                                      20
```

LIPOSOMES FOR TARGETING TUMOR-ASSOCIATED MACROPHAGES

CROSS-REFERENCE TO RELATED APPLICATIONS

This application is a national phase entry under 35 U.S.C. § 371 of International Patent Application PCT/NL2019/050170, filed Mar. 20, 2019, designating the United States of America and published as International Patent Publication WO 2019/182441 A1 on Sep. 26, 2019, which claims the benefit under Article 8 of the Patent Cooperation Treaty to European Patent Application Serial No. 18162956.9, filed Mar. 20, 2018.

TECHNICAL FIELD

The disclosure relates to liposome formulations for use in cell type specific targeting of the liposome and liposome associated compounds such as drugs. The disclosure, in particular, relates to liposome formulations for targeting of tumor-associated macrophages. Inclusion of a phospholipid with a C-terminal carboxyl or carboxaldehyde in a liposome preferably in a certain ratio to other constituents of the liposome can lead to their specific interaction with particular macrophages such as M2 macrophages (also known as anti-inflammatory or tumor-inducing macrophages).

BACKGROUND

The tumor microenvironment (TME) contains a variety of nonmalignant cell types in addition to malignant tumors cells. The majority of the nonmalignant cells include stromal cells such as tumor-associated macrophages (TAMs), fibroblasts, and tumor vasculature cells. TAMs promote key processes in tumor progression, like angiogenesis, immunosuppression, invasion, and metastasis [1]. In tumors, M2 macrophages are the activated form of macrophages, which compose most of the TAMs. They promote angiogenesis, suppress the immune system, and enhance chemoresistance, thus limiting efficacy of chemotherapy [2]. Therefore, specific inhibition of pro-tumoral activities of M2 macrophages within the TME represents a promising strategy contributing to the fight against cancer.

Depleting macrophages or blocking the recruitment of monocytes using bisphosphonates or colony stimulating factor receptor (CSF-1) inhibitor, respectively, led to inhibition of tumor growth and metastasis (Pyonteck et al. 2013 *Nat. Med.* 19(10): 1264-72) (Sabatino et al. 2014 *PloS One* 9 e101260, doi:10.1371/journal.pone.0101260). Recently, Postma et al., showed that targeting of the STAT6 pathway with AS1517499 inhibited TAMs by decreasing M2 expression markers, and tumor migration. Interestingly, AS1517499 attenuated the tumor growth and early liver metastasis in a 4T1 orthotopic tumor model (Binnemars-Postma et al. 2018 *FASEB J.* 32, 969-978 doi:10.1096/fj.201700629R). Another strategy is to activate M1-type macrophages or switch of M2 macrophages toward M1 phenotype using Mifamurtide (MTP-PE) that has potent monocyte/macrophage-activating properties (Meyers et al. 2014 *Adv. Exp. Med. Biol.* 804, 307-321, doi:10.1007/978-3-319-04843-7_17) (Aasano et al. 1993 *J. Immunother. Emphasis Tumor Immunol.* 14, 286-292) (Maeda et al. 1991 *Cancer Commun.* 3, 313-321). MTP-PE results from the covalent addition of alanine and dipalmitoyl phosphatidylethanolamine (PE) to muramyl dipeptide; the phospholipid (PE) facilitates incorporation of the peptide into the lipid layer of liposomes. MTP-PE induces activation of M1-type macrophages and secretes numerous cytokines, including TNF$\alpha$, Interleukin (IL-6, IL-1$\beta$)(Maeda et al. 1991 *Cancer Commun.* 3, 313-321) (Maeda et al. 1993 *Cancer Immunol. Immunother.* 37, 203-208). On the other hand, Interferon (IFN)-$\gamma$ a well-known cytokine, activates inflammatory M1-type macrophages via the Jak-STAT1 signaling pathways (Sica et al. 2012 *J. Clin. Invest.* 122, 787-795, doi:10.1172/JCI59643).

Liposomes are the most commonly used drug carrier to deliver drugs to tumors. Many liposomal formulations such as Myocet® (non-PEGylated formulation of doxorubicin), Doxil® (Pegylated liposomal formulation of doxorubicin), DaunoXome® (Pegylated liposomal formulation of daunorubicin) and Marqibo® (liposomal formulation of vincristine sulfate) have been used clinically for the treatment of different cancer types. Liposome-enabled tumor targeting is mainly based on the principal of passive targeting that relies on the phenomenon called the Enhanced Permeability and Retention (EPR) effect.

Macrophages express different phagocytosis receptors such as pattern-recognizing receptors (e.g., mannose receptor), opsonic receptors and scavenger receptors (e.g., CD36) [3]. To target some of these receptors, many approaches such as surface modifications with mannose sugar, targeting peptides or monoclonal antibodies have been proposed to induce uptake of nanoparticles by macrophages [4, 5]. Oxidized phospholipids have been shown to interact with macrophages through CD36 receptor [6]. In order to target M2 macrophages specifically, it is important to understand the differences in uptake behavior by these cell types. In previous studies, specific phagocytosis receptors have been identified, which are up-regulated in M2 macrophages [7]. By investigating their endogenous ligands, three different receptors involved in the recognition of oxidized lipids were identified: the scavenger receptor class B member 1 (Scarb1), collectin subfamily member 12 (Colec12) and the already mentioned CD36 receptor [7]. All three receptors belong to the class of scavenger receptors [8].

Unsaturated lipids are unstable and may oxidize into different derivatives [9, 10]. Moreover, oxidized lipids may result in toxicity or activation of macrophages [11-16]. Therefore, saturated phospholipids were selected, which have a carboxyl or carbonyl at one chain, here called phospholipids with a C-terminal carboxyl or carboxaldehyde group. In one aspect, the disclosure provides M2 macrophage-targeted liposomes comprising phosphatidylcholine with a C-terminal carboxyl or carboxaldehyde group (CyPC) in their lipid composition, which can be potentially used for drug delivery purposes.

Unilamellar liposomes were prepared using a carrier lipid, i.e., phosphatidylcholine in combination with the carboxylated forms of lipids. Different amounts of CyPC lipids were incorporated into the liposomes to optimize their binding to and uptake into M2 macrophages. Their toxicity and effect on gene expression of macrophages was evaluated. Their macrophage specificity was tested in vitro, in vivo, their tumor accumulation and organ distribution were evaluated. Furthermore, the role of the overexpressed receptors in the specific uptake of carboxylated-lipid containing liposomes by M2 macrophages was investigated. The specific binding and uptake of M2 targeted liposomes into M2 differentiated macrophages compared to the M1 phenotype has been developed and demonstrated. This M2 targeted liposomes is composed of carboxylated phospholipids, i.e., 1-palmitoyl-2-azelaoyl-sn-glycero-3-phosphocholine (PAzPC), Hydrogenated soy phosphatidylcholine (HSPC), and cholesterol.

Finally, in-vitro, it has been confirmed that the liposomes of the disclosure are specifically internalized by M2-type macrophages compared to M1-type with fluorescent microscopy and flow cytometry analyses.

BRIEF SUMMARY

The disclosure provides a composition comprising a liposome for use in a method of treating cancer, chronic inflammation, an autoimmune disease, fibrosis, a brain disorder, wherein the liposome comprises a first phospholipid comprising a $C_{14}$-$C_{19}$:0 fatty acid and a $C_3$-$C_{15}$:0 fatty acid with a C-terminal carboxyl or a carboxaldehyde group; a second phospholipid comprising a $C_{14}$-$C_{19}$:0 fatty acid and a $C_{14}$-$C_{19}$:0 fatty acid and a sterol.

Also provided is a composition comprising a liposome comprising a first phospholipid comprising a $C_{14}$-$C_{19}$:0 fatty acid and a $C_3$-$C_{15}$:0 fatty acid with a C-terminal carboxyl or a carboxaldehyde group; a second phospholipid comprising a $C_{14}$-$C_{19}$:0 fatty acid and a $C_{14}$-$C_{19}$:0 fatty acid and a sterol, the first phospholipid is preferably a phosphatidylcholine; the second phospholipid is preferably HSPC and the sterol is preferably cholesterol, wherein preferably the molar ratio of the respective ingredients is 2-3:5-6:2-3; preferably 2:6:2; or 3:5:2, respectively.

In one aspect the disclosure provides a composition comprising a liposome for use in preferentially providing tumor-associated M2 macrophages with a compound comprised in the liposome in the treatment of cancer, wherein the liposome comprises the compound, a first phospholipid comprising a $C_{14}$-$C_{19}$:0 fatty acid and a $C_3$-$C_{15}$:0 fatty acid with a C-terminal carboxyl or a carboxaldehyde group; a second phospholipid comprising a $C_{14}$-$C_{19}$:0 fatty acid and a $C_{14}$-$C_{19}$:0 fatty acid and a sterol.

Further provided is a composition comprising a labelled liposome for use in preferentially labeling tumor-associated M2 macrophages in an individual, wherein the liposome comprises a first phospholipid comprising a $C_{14}$-$C_{19}$:0 fatty acid and a $C_3$-$C_{15}$:0 fatty acid with a C-terminal carboxyl or a carboxaldehyde group; a second phospholipid comprising a $C_{14}$-$C_{19}$:0 fatty acid and a $C_{14}$-$C_{19}$:0 fatty acid, a sterol and a label.

The first phospholipid is preferably a phosphatidylcholine (first phosphatidylcholine). The second phospholipid is preferably a phosphatidylcholine (second phosphatidylcholine). The sterol is preferably cholesterol.

The disclosure also provides a composition comprising a liposome comprising an oxidized phospholipid, a hydrogenated phospholipid and a sterol.

Further provided is a composition comprising a liposome for use in a method of treating cancer, wherein the liposome comprises an oxidized phospholipid; a hydrogenated phospholipid and a sterol.

Also provided is a composition comprising a liposome for use in preferentially providing tumor-associated M2 macrophages with a compound comprised in the liposome in the treatment of cancer, wherein the liposome comprises the compound, an oxidized phospholipid, a hydrogenated phospholipid and a sterol, preferably the compound, an oxidized phosphatidylcholine; a hydrogenated phosphatidylcholine (preferably HSPC) and a sterol.

In one aspect, the disclosure provides a composition comprising a labelled liposome for use in preferentially labeling tumor-associated M2 macrophages in an individual, wherein the liposome comprises an oxidized phospholipid, a hydrogenated phospholipid, a sterol and a label.

The oxidized phospholipid is preferably an oxidized phosphatidylcholine. The hydrogenated phospholipid is preferably a hydrogenated soybean phosphatidylcholine (HSPC). The sterol is preferably cholesterol.

The disclosure also relates to the use of a composition as described herein for targeting liposomes to M2 macrophages The disclosure provides a method of treating cancer, chronic inflammation, an autoimmune disease, fibrosis, a brain disorder, the method comprising administering an effective amount of the composition of the disclosure.

In one aspect, the method of treatment provided by the disclosure entails contacting a cell, preferably a tumor-associated M2 macrophage, with the liposomes of the disclosure, preferably containing PAzPC.

Also included in the method of treatment is the composition of the disclosure wherein the liposomes contain a drug, comprising; AS1517499; MTP-PE and IFNγ as well as a composition of the disclosure, wherein the liposome contains a combination of drugs, comprising; AS1517499; MTP-PE and IFNγ, preferably a combination of MTP-PE and IFNγ.

Further provided in the method of treatment is a composition of the disclosure, wherein the liposome contains a carrier for hydrophobic drugs, preferably cyclodextrin.

The disclosure also provides a method of repolarizing M2 macrophages to M1 macrophages, the method comprising contacting a cell, preferably a tumor associated M2 macrophage, with an effective amount of the composition of the disclosure.

In one aspect, the method applies the composition of the disclosure, wherein the liposome contains a drug, comprising; AS1517499; MTP-PE and IFNγ as well as a combination of drugs, comprising; AS1517499; MTP-PE and IFNγ, preferably a combination of MTP-PE and IFNγ.

Further comprised in the method is the liposome of the disclosure containing a carrier for hydrophobic drugs, preferably cyclodextrin.

The method also employs the liposome of the disclosure containing a molecule that is capable of inducing repolarization of an M2 macrophage to an M1 macrophage comprising; one or more cytokines; one or more bacterial products; one or more TLR-agonists; one or more miRNAs or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
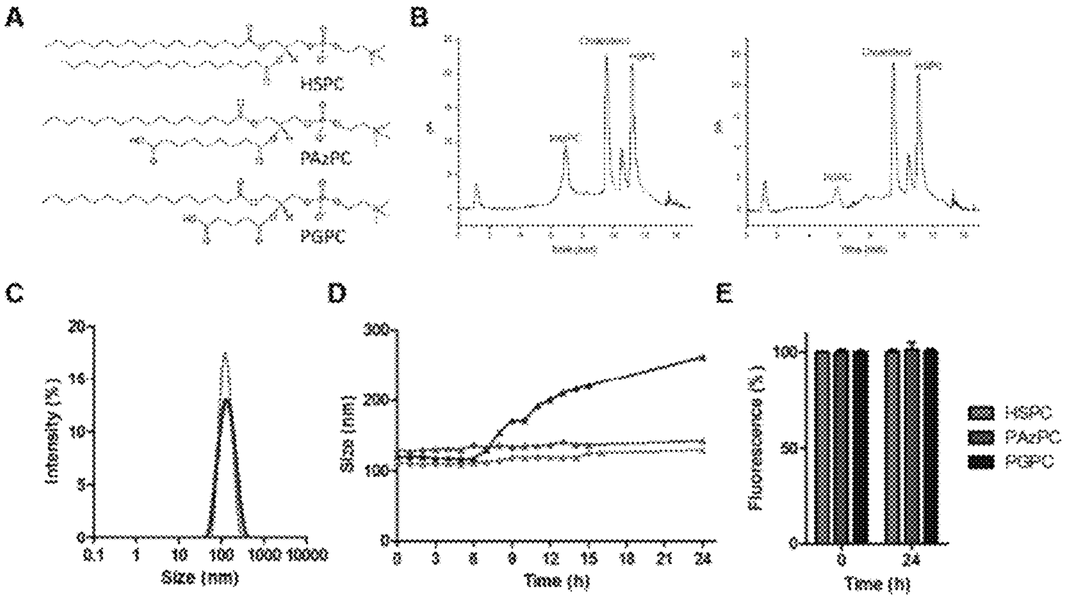
FIG. 1: Preparation and analysis of CyPC-containing liposomes. (A) Structure of selected lipids (B) Typical chromatogram of lipid mixtures analyzed using uHPLC separation with corona CAD. (C) Representative DLS graphs showing size distribution of different liposomal preparations (D) Stability of liposomes in culture medium at 37° C. for 24 hours. (E) Fluorescence of liposomes before and after incubation in culture medium at 37° C. for 24 hours. Molar ratio CyPC:HSPC:Cholesterol 0:8:2 (HSPC) and 5:3:2 (PAzPC and PGPC) were used in panels C-E.

A liposome is a spherical vesicle having at least one lipid bilayer. The liposome can be used as a vehicle for administration of nutrients, labels and pharmaceutical drugs to biological systems and cells, in particular. Liposomes can be prepared by disrupting biological membranes (such as by sonication) or be generated artificially from mixtures of the lipids and water. Liposomes for clinical use have been reviewed by Akbarzadeh et al. in *Nanoscale Res Lett.* 2013; 8(1): 102 (doi:10.1186/1556-276X-8-102). Liposomes of the disclosure are preferably 50% or more unilamellar liposomes, preferably 60% or more, preferably 70%, 80% or 90% or more unilamellar liposomes. These can be prepared in various ways. Some of these are described in Akbarzadeh et al. and references therein. The liposomes are preferably 30-200 nanometer (nm), preferably 50-200 nm, preferably 80-115 nm. The size distribution is preferably such that a liposome composition has more than 80%, preferably more than 90% of the liposomes particles in the range indicated, i.e., 30-200 nm; 50-200 nm; or 80-115 nm. A liposome of the disclosure can be combined with one or more other liposomes having a different size. The size in nanometers of a (near) spherical liposome is the diameter of the narrowest distance between opposite outer ends of the outer membrane of the liposome. The liposome is preferably a unilamellar liposome.

Liposomes of the disclosure comprising one or more carboxylated lipids are well-defined lipid molecules and can be applied for the development of clinical products. The combination of liposomes and carboxylated lipids can be used for drug encapsulation and delivery in a clinical setting. However, in the disclosure, it has been found that such liposomes also inhibit the growth and/or metastasis of a cancer in vivo. This property can be enhanced significantly be incorporating one or more compounds as defined herein into the liposomes. A liposome of the disclosure can inhibit the formation of a pre-metastatic niche in tissue of the individual. It preferably inhibits the formation of a pre-metastatic niche in the liver of an individual.

Successfully encapsulating the stat6 inhibitor AS1517499 into TAM targeted PAzPC-liposomes has been demonstrated, which inhibited metastatic niche formation in lungs in 4T1 breast tumor model. Furthermore, it has been found that MTP-PE transforms macrophages into M1 type, anti-tumoral macrophage. Interestingly, incorporation of MTP-PE into PAzPC-liposomes was successfully performed and led to the specific uptake by M2 macrophages. These data indicate that using the TAM-targeted liposomes MTP-PE and IFNγ can be delivered to TAMs and potentially used for re-polarization into M1 macrophages.

The liposome preferably comprises a compound. The compound is preferably drug or a label. The compound can be a small molecule, a peptide, a lipid, a cytokine or a combination thereof. The compound is preferably a hydrophilic compound. The compound can also be hydrophobic. A hydrophobic compound can be (partly) present in the membrane of the liposome and/or be complexed with a solubilizer such as a cyclodextrin (see Drug-in-cyclodextrin-in-liposomes: A novel drug delivery system for flurbiprofen (Zhang et al. 2015. *Int. J. Pharm.* 492(1-2):40-5. Doi: 10.1016/j.ijpharm.2015.07.011). Various types of compounds can be used in liposomes. Examples are mentioned in Binnemars-Postma et al. (2017. *Int. J. Mol. Sci.* 18, 979; doi 10:3390/ijms18050979 and references therein). Non-limiting examples are simvastatin and alendronate and doxorubicin. Other compounds are Colony stimulating factor receptor-1 (CSF-1R) inhibitors: such as but not limited to PLX3397, BLZ945 and GW2580; Stat6 inhibitors: such as but not limited to AS1517499, TMC-264 and the active metabolite of leflunomide (A771726); Stat3 inhibitors: such as but not limited to sorafenib or sunitinib; Clodronate or zoledronic acid, trabectedin; inhibitor of macrophage migration factor: 4-iodo-6-phenylpyrimidine (4-IPP); and/or muramyl tripeptide-phosphatidyl ethanolamine. The compound can be a protein, a nucleic acid molecule such as a nucleic acid molecule that encodes a protein, such as CAS9. The compound can be an mRNA, an oligonucleotide, preferably an antisense oligonucleotide, an siRNA, a miRNA, a splice modulating oligonucleotide, a gapmer, a CRISPR, or an lnRNA.

The liposome can comprise two or more compounds. For instance, a guide RNA, CAS9 and a repair DNA for integration/homologous recombination into the target nucleic acid.

A label is preferably a label that can be visualized in vivo in a non-invasive manner. The label is preferably a radioactive label or an infrared label.

The disclosure provides a composition comprising a liposome for use in a method of treating cancer, chronic inflammation, an autoimmune disease, fibrosis, a brain disorder, wherein the liposome comprises a first phospholipid comprising a $C_{14}$-$C_{19}$:0 fatty acid and a $C_3$-$C_{15}$:0 fatty acid with a C-terminal carboxyl or a carboxaldehyde group; a second phospholipid comprising a $C_{14}$-$C_{19}$:0 fatty acid and a $C_{14}$-$C_{19}$:0 fatty acid and a sterol. $C_{14}$-$C_{19}$ means that the fatty acid in the phospholipid can have 14, 15, 16, 17, 18, or 19 carbon atoms until the oxygen of the ester linkage to the glycerol backbone. It preferably has 15-19 carbon atoms, preferably 16-19 more preferably 16 or 17, preferably 16. $C_3$-$C_{15}$ analogously means that the fatty acid in the phospholipid can have 3-15 carbon atoms until the oxygen of the ester linkage to the glycerol backbone. It preferably has 4, 5, 6, 7, 8, 9, 10, 11, 12 carbon atoms until the oxygen of the ester linkage, preferably 5-10, more preferably 5-8. In a preferred embodiment, the phospholipid has 5 or 8, preferably 8 carbon atoms until the oxygen of the ester linkage. The $C_3$-$C_{15}$ phospholipid has a carboxyl or a carboxaldehyde group at the C-terminal end of the fatty acid, i.e., the end opposite to the oxygen of the ester linkage. The carboxyl group has the structural formula —COOH and a carboxaldehyde group has the structural formula —CHO consisting of a carbonyl center (a carbon double-bonded to oxygen) with the carbon atom also bonded to hydrogen and to the next carbon atom of the fatty acid. The carbon atom of the carbonyl center and the carbon of the COOH group are part of the numbering the carbon atoms in the fatty acid of the phospholipid. The $C_{14}$-$C_{19}$ fatty acid is preferably on the carbon 1 of the glycerol backbone. The $C_3$-$C_{15}$ fatty acid is preferably on the carbon 2 of the glycerol backbone. The :0 notation indicates that there are no double bonds in the fatty acid chain. In some embodiments, the liposome(s) of the disclosure do not contain an unsaturated phospholipid, especially PlinPC (16:0-18:2).

The disease is preferably cancer, chronic inflammation, an autoimmune disease, fibrosis, or a brain disorder. The cancer is preferably a solid tumor, preferably lung cancer, breast cancer, prostate cancer, brain cancer, liver cancer, pancreatic cancer, or renal cancer. The autoimmune disease is preferably Rheumatoid arthritis, anti-Glomerular Basement Membrane nephritis, autoimmune hepatitis, Alopecia Areata, Psoriasis, Graves' disease, or Fibromyalgia.

The first, second or both phospholipids are preferably phosphatidylcholines. Phosphatidylcholines (PC) are a class of phospholipids that incorporate choline as a headgroup. The first phosphatidylcholine is preferably 1-palmitoyl-2-(5'-oxo-valeroyl)-sn-glycero-3-phosphocholine (POVPC), 1-palmitoyl-2-(9'-oxo-nonanoyl)-sn-glycero-3-phosphocholine (PoxnoPC), 1-palmitoyl-2-glutaryl-sn-glycero-3-phosphocholine (PGPC), 1-palmitoyl-2-azelaoyl-sn-glycero-3-phosphocholine (PAzPC), or a combination thereof.

The second phosphatidylcholine is preferably dipalmitoyl-phosphatidylcholine (DPPC); distearoylphosphatidylcholine (DSPC); a hydrogenated soybean phosphatidylcholine (HSPC) or a combination thereof.

A representative $C_{18}$-$C_{18}$ phosphatidylcholine is indicated herein below.

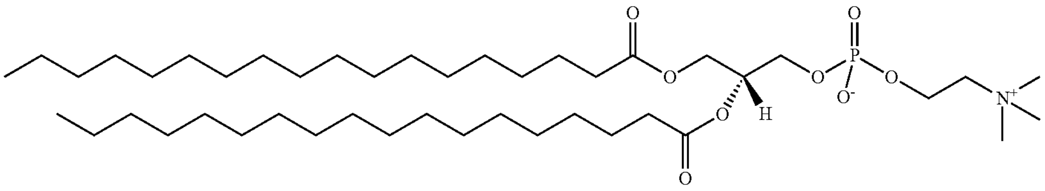

Representative structure only.
This structure is only one of many possible structures in the product The liposome is preferably comprised in an isotonic solution; preferably a physiological salt solution. Typically the pH is around the pH of the blood of a normal individual. The pH can be buffered if needed. The hydrophilic interior of the liposome can be different from the solution it is comprised in. Typically the interior solution is also an isotonic solution with a pH around the pH of the blood. A pH around the pH of the blood is a pH of 7.35-7.45. Considering the small volume of the liposome or the injection fluid the pH of both is not very critical. The pH of a solution in or around the liposome can be 6-8 or even have another pH all together. The administration can be intravenous, subcutaneous, intraperitoneally or other administration all together such as intra-organ, in the brain, or in the spinal fluid. The liposome can be contained in a gel, for instance, as a slow release formula.

The sterol is preferably cholesterol.

The first phosphatidylcholine; the second phosphatidylcholine and sterol are preferably present in a molar ratio of 0.5-8:1.5-24:0.5-8, respectively; preferably 1-4:3-12:1-4; preferably 1.5-2.5:4.5-7.5:1.5-2.5; or preferably 2-3:5-6:2-3.

A preferred liposome of the disclosure comprises PAzPC; HSPC and cholesterol, preferably in a molar ratio of 2-3:5-6:2-3, respectively; and preferably in a molar ratio of 2:6:2; or 3:5:2, respectively.

Another preferred liposome of the disclosure comprises PGPC; HSPC and cholesterol, preferably in a molar ratio of respectively 2-3:5-6:2-3; and preferably in a molar ratio of respectively 2:6:2; or 3:5:2.

The first phosphatidylcholine comprises preferably comprises POVPC; PoxnoPC; PGPC; PAzPC, or a combination thereof.

Liposomes are most often composed of phospholipids, especially phosphatidyl-choline, but may also include other lipids, such as egg phosphatidylethanolamine, so long as they are compatible with a lipid bilayer structure. A lipid bilayer is herein also referred to as a membrane. When used as such the term herein is used to refer to lipid bilayers. It is specifically mentioned when other types of membranes are intended.

Liposomes of the disclosure preferably comprise as membrane components an oxidized phospholipid, a hydrogenated phospholipid and a sterol. The outer lipid membrane of a liposome of the disclosure preferably consists of an oxidized phospholipid, a hydrogenated phospholipid and a sterol. The ingredients are preferably present in specific molar ratios. In a preferred embodiment, the specific molar ratio is the range of 2-3 for the oxidized phospholipid; the range 5-6 for the hydrogenated phospholipid and the range of 2-3 for the sterol. The molar ratio of oxidized phospholipid:hydrogenated phospholipid:sterol is preferably 2-3:5-6:2-3. The molar ratio is preferably 2:6:2; or 3:5:2. The molar ratios are the same as the preferable ingredients such as the oxidized phosphatidylcholine, the hydrogenated phosphatidylcholine and/or the cholesterol.

The oxidized phospholipid is preferably an oxidized phosphatidylcholine. The hydrogenated phospholipid is preferably a hydrogenated phosphatidylcholine. The sterol is preferably cholesterol.

In a preferred embodiment, the oxidized phospholipid is an oxidized phosphatidylcholine, the hydrogenated phospholipid is a hydrogenated phosphatidylcholine and the sterol is cholesterol. Such a liposome comprises as membrane components an oxidized phosphatidylcholine, a hydrogenated phosphatidylcholine and cholesterol.

The oxidized phosphatidylcholine is preferably 1-palmitoyl-2-(5'-oxo-valeroyl)-sn-glycero-3-phosphocholine (POVPC), 1-palmitoyl-2-(9'-oxo-nonanoyl)-sn-glycero-3-phosphocholine (PoxnoPC), 1-palmitoyl-2-glutaryl-sn-glycero-3-phosphocholine (PGPC), 1-palmitoyl-2-azelaoyl-sn-glycero-3-phosphocholine (PAzPC), or a combination thereof. In a preferred embodiment, it is PAzPC or PGPC, preferably PAzPC. Where PGPC stimulates higher uptake of the liposome and associated compound, PAzPC is more selective, also at good but suboptimal ratios. Where PGPC liposomes appear to become less selective for M2 macrophages at suboptimal ratios.

Polyethylene glycol (PEG) can be introduced into this liposomal formulation to enhance circulation while maintaining the targeting affinity toward target cells. Sheddable PEG can also be used, when it is conjugated to a phospholipid with cleavable linker (for example, dithiol, hydrazone, ester, benzoic imine, peptide linkages) so that PEG can shed off when get exposed to the right environment (for example, low pH, high glutathione, or proteases) and allow liposomes to interact with M2 macrophages. Sheddable PEG may also include ceramide-PEG.

A peptide is a compound having two or more amino acids linked in a chain, the carboxyl group of each acid being joined to the amino group of the next by a peptide bond of the type —OC—NH—. A peptide typically contains up to 25 amino acids in peptide linkage. A protein or polypeptide typically comprises 26 or more amino acid residues in peptide linkage. A peptide is typically though not necessarily a single chain. A protein or polypeptide can have one, two or more chains that are held together by non-covalent bonds and/or one or more disulfide bonds.

An M1 macrophage is activated, typically by IFN-γ or lipopolysaccharide (LPS), and produce proinflammatory cytokines, phagocytize microbes, and initiate an immune response. M1 macrophages produce nitric oxide (NO) or reactive oxygen intermediates (ROI) to protect against bacteria and viruses.

M2 macrophages are activated by exposure to certain cytokines such as IL-4, IL-10, or IL-13. M2 macrophages can produce either polyamines to induce proliferation or proline to induce collagen production. These macrophages are associated with wound healing, tissue repair and are not desired in a cancer setting.

Inducing a change from a typical M2 macrophage into a macrophage with M1 properties is also referred to as repolarization. A liposome of the disclosure can stimulate the repolarization of an M2 macrophage. It can do so on its own. However, a liposome of the disclosure typically contains a compound such as a small molecule, peptide and/or cytokine that has the property to induce the depolarization. Examples of such compounds are mentioned herein. Many alternatives are known in the art.

For the purpose of clarity and a concise description features are described herein as part of the same or separate embodiments, however, it will be appreciated that the scope of the disclosure may include embodiments having combinations of all or some of the features described.

Where a range is indicated herein, it includes the numbers identifying the range. For instance, a range of 1-2.5 includes the numbers 1 and 2.5.

EXAMPLES

Materials and Methods

Preparation of Liposomes

Liposomes were prepared using the ethanol injection technique [17]. Briefly, hydrogenated soybean phosphatidylcholine (HSPC, Lipoid GMBH, Germany), carboxylated lipids 1-palmitoyl-2-azelaoyl-sn-glycero-3-phosphocholine (PAzPC, Cayman chemicals, Ann Arbor, MI) or 1-palmitoyl-2-glutaryl phosphatidylcholine (PGPC, Cayman chemicals), cholesterol (Sigma Aldrich) and the lipophilic fluorescent label 1,1'-Dioctadecyl-3,3,3',3'-tetramethylindocarbocyanine perchlorate (DiI, Sigma Aldrich, St Louis, MO) at a molar ratio of 0.1 of total lipid were dissolved in ethanol and heated at 70° C. The heated lipid solution was injected into PBS to create a crude liposomal formulation with a concentration of 10 mM total lipid, which was then diluted to 2.5 mM total lipid. The crude liposomal formulation was extruded using the Avestin Liposofast extruder. After preparation, liposomes were dialyzed against PBS using 10 kD cutoff slide-A-lyzers (Thermo Fisher Scientific, Waltham, MA). Liposomal size (in PBS) and zeta potential (in 0.1 mM KCl) were measured using Zetasizer Nano ZS (Malvern, Malvern, UK). Liposomes were prepared using different molar ratios of CyPC:HSPC:Cholesterol.

For inclusion of drugs into liposomes, AS1517499 (Manufacturer) was dissolved in DMSO, and subsequently dissolved in 10% 2-hydroxypropyl-β-cyclodextrin solution for encapsulation of AS1517499, followed by incorporation of this mixture into liposomes.

Liposome Analysis

Concentration and composition of the liposomes were analyzed using the UltiMate® 3000 UHPLC with Charged Aerosol Detector (Dionex™ Corona™; Thermo Scientific) using an Acquity UPLC BEH C18 column (130 Å, 1.7 µm, 2.1 mm×50 mm). The binary mobile phase consisted of (A) methanol with 0.05% TFA, and (B) methanol:water (80:20 v/v) with 0.05% TFA, and a constant flow rate of 0.2 ml/minute. Data was analyzed using Chromeleon® Chromatography Data System. Calibration curves were prepared in the range 6-200 µg/ml for all lipids. Before analysis, liposomes were diluted ten times in methanol and placed in an ultrasonic waterbath for 30 minutes.

To measure drug encapsulation into the liposomes, dialyzed liposomes were dissolved in methanol and vortexed thoroughly. Subsequently, samples were centrifuged at 13k rpm for 10 minutes. This was followed by measurement of the samples at 261 nm and 306 nm using an ND-1000 spectrophotometer (NanoDrop, Thermo Fisher Scientific). Sample concentration was determined using (AS15117499) calibration curves.

Liposome Stability

Liposomes were diluted ten times in cell culture medium without serum and incubated at 37° C. for 24 hours. Size was determined using the Zetasizer Nano ZS (Malvern). For loss of fluorescence, undiluted samples were incubated in Amicon Ultra tubes (Mw cut-off 30 kD, Sigma Aldrich) in a container containing cell culture medium without serum. Fluorescence of samples was determined before and after incubation using the Tecan Infinite 200 Pro (Männedorf, Switzerland).

Cell Culture

Monocytic human THP-1 cells (ATCC, Rockville, MD) were cultured in suspension in RPMI-1640 medium supplemented with 10% FBS (Lonza, Basel, Switzerland), 100 U/ml penicillin, 0.1 mg/ml streptomycin (Sigma Aldrich, St Louis, MO) and 2 mM L-glutamine (GE Healthcare, Little Chalfont, UK) in a $CO_2$ incubator at 37° C. Murine bone marrow derived macrophages (BMDMs) were isolated from male C57BL6 mice by flushing the femur and tibia with PBS under sterile conditions. The bone marrow cells were then resuspended in RPMI-1640 medium supplemented with 1% L-glutamine, 1% Penicillin and streptomycin, 20% FBS and 20% 3T3-conditioned medium (filter-sterilized). The cells were then incubated for 10 days at 37° C. and 5% CO2 with medium change every 3-4 day. 4T1 tumor cells were cultured in RPMI-1640 medium supplemented with 10% FBS, 100 U/ml penicillin, 0.1 mg/ml streptomycin and 2 mM L-glutamine in a $CO_2$ incubator at 37° C.

Macrophage Differentiation

Macrophages were differentiated as reported in [7]. Briefly, THP-1 cells were treated for 24 hours with 100 ng/ml of phorbol 12-myristate 13-acetate (PMA, Cayman Chemicals) to allow their attachment. The medium was replaced by medium containing 20 ng/ml IL-4 and IL-13 (Peprotech, London, UK) for M2 differentiation, or 20 ng/ml IFNγ (Peprotech) and 100 ng/ml LPS (Sigma Aldrich) for M1 differentiation. Cells were incubated with cytokines for 24 hours (gene expression on differentiation), and 72 hours (liposome uptake experiments). BMDMs were plated overnight with a density of 50,000 cells/ml. After 24 hours, medium was aspirated. Cells were incubated for 24 hours in complete RPMI medium containing IL-4 and IL-13 at 10 ng/ml (M2 differentiation) or LPS and IFN-γ at 100 and 10 ng/ml. In case of RAW264.7 cells, M1 macrophages were differentiated using 10 ng-mL murine recombinant IFNγ and 10 ng-mL LPS. M2 macrophages were differentiated using 10 ng-mL murine IL-4 and IL-13.

Macrophage Transfection $0.25\times10^6$ cells were plated in a 24-well plate and activated as described above. siRNA (CD36, Colec12, Scarb1, Thermo Fisher Scientific) complexes using HiPerfect Transfection reagent (Qiagen, Venlo, The Netherlands) were prepared as per manufacturer's instructions. siRNA was added to the cells at a concentration of 150 nM for 4 hours, after which complexes were removed and cells were differentiated as described above. Cells were lysed 6 and 24 hours after cytokine differentiation for PCR analysis. For quantitative liposome uptake experiments, cells were used 44 hours after cytokine differentiation.

Quantitative Real Time PCR $0.5\times10^6$ RAW264.7/THP-1 cells were plated in 12-well plates, if applicable treated with respective cytokines for differentiation, and activated using PMA. Cells were then incubated with different liposomal preparations (50 µM) or differentiation cytokines for 24 hours. BMDM were differentiated as described above. After differentiation, cells were washed with PBS and then lysed using lysis buffer and total RNA was isolated using SV Total RNA Isolation System (Promega, Madison, WI). cDNA was prepared by using iScript cDNA synthesis kit (Bio-Rad, Hercules, CA) and qRT-PCR was performed with 10 ng of cDNA per reaction mixture using SYBR green assay (Bioline, London, UK). Primer sequences are listed in Table 1. Reactions were measured using the CFX384 Real-Time PCR detection system (Bio-Rad). The threshold cycles (Ct) values were calculated and relative gene expression (ddCt method) was analyzed after normalization using the Rsp18 (THP-1) or Gapdh (RAW264.7/BMDM) house-keeping gene.

Quantitative Liposome Uptake

Liposomes were diluted to equal fluorescence at a maximum concentration of 250 µM lipid (THP-1) or 125 µM (BMDM) in culture medium without serum and added to differentiated macrophages and incubated at 37° C. for 2 hours (THP-1) or 30 minutes (BMDM). After incubation, cells were vigorously washed, immediately placed on ice and then detached using Accutase cell detachment solution (Sigma Aldrich) and gentle scraping. Cells were then collected and particle uptake was assessed by measuring mean fluorescence intensities in the FL-2 channel for at least 10,000 gated cells, using flow cytometry (BD FACSCalibur, Becton Dickinson, Franklin Lakes, NJ). Gates were set in the FSC vs SSC plot, using untreated control cell populations. For all experiments, identical settings were used. Data was analyzed using Flowing Software 2.5.0.

Toxicity of CyPC Liposomes $5\times10^4$ TIP-1 cells per well were seeded in a 96-well plate and activated using PMA as described above. Cells were then incubated in the absence of serum for 24 hours with different liposomal preparations (50 µM). After 24 hours, medium was removed, cells were washed once with PBS, and a 10% 110 µg/ml Resazurin sodium salt solution (Sigma Aldrich) was added. Cells were allowed to incubate for an additional 75 minutes, after which the Resazurin solution was transferred to a black 96-well plate and fluorescence was measured using the Victor3 plate reader.

TABLE 1

Primer sequences of selected human (h) and murine (m) genes.

| Gene | SEQ. ID No: | Forward (5'→3') | SEQ. ID No: | Reverse (3'→5') | Accession |
|---|---|---|---|---|---|
| Arg-1 (m) | 1 | *GTGAAGAACCCACGGTCTGT* | 2 | *CTGGTTGTCAGGGGAGTGTT* | *NM_007482.3* |
| Cd36 (h) | 3 | TGGCAACAAACCACACACTG | 4 | AAGTCCTACACTGCAGTCCTC | NM_000072.3 |
| Colec12 (h) | 5 | AGGTCGAGGTTAGACACTGAAG | 6 | GATCCTCTGTCACCTCTTGGAC | NM_130386.2 |
| Dc-sign (h) | 7 | GAACTGGCACGACTCCATCA | 8 | CTGGAAGACTGCTCCTCAGC | NM_001144897.1 |
| Dectin-1 (h) | 9 | ATGGCTCTGGGAGGATGGAT | 10 | GGGCACACTACACAGTTGGT | NM_197947.2 |
| Gapdh (m) | 11 | *ACAGTCCATGCCATCACTGC* | 12 | *GATCCACGACGGACACATTG* | *XM_001476707.3, XM_001479371.4, XM_003946114.1, NM_008084.2* |
| Il-1β (h) | 13 | CAGAAGTACCTGAGCTCGCC | 14 | AGATTCGTAGCTGGATGCCG | NM_000576.2 |
| Il-6 (h) | 15 | TGCAATAACCACCCCTGACC | 16 | ATTTGCCGAAGAGCCCTCAG | NM_000600.3 |
| Il-6 (m) | 17 | *TGATGCTGGTGACAACCACGGC* | 18 | *TAAGCCTCCGACTTGTGAAGT GGTA* | *NM_031168.1* |
| Rps18 (h) | 19 | TGAGGTGGAACGTGTGATCA | 20 | CCTCTATGGGCCCGAATCTT | NM_022551.2 |
| Scarb1 (h) | 21 | AAGATTGAGCCTGTGGTCCTG | 22 | CCTCCTTATCCTTTGAGCCCT | NM_005505.4 |
| Tnf-α (h) | 23 | CTTCTGCCTGCTGCACTTTG | 24 | GTCACTCGGGGTTCGAGAAG | NM_000594.3 |

Microscopy Analysis of Liposome Uptake $0.5\times10^6$ THP-1 cells per well were seeded in a 12-well plate and differentiated as described above. Fluorescence of different liposomes was measured in PBS, using the Victor3 multilabel fluorescence plate reader (Perkin Elmer, Waltham, MA). Liposomes were diluted to equal fluorescence at a maximum concentration of 250 µM lipid in culture medium without serum and incubated for 2 hours. After incubation, cells were vigorously washed and fixed during 20 minutes using 4% formalin. Cells were washed 2 times in PBS and mounted in mounting medium with DAPI. Uptake of liposomes was visualized using the inverted fluorescent microscope EVOS (Applied Biosystems). Images were taken at 40× magnification using identical settings.

Liposome Distribution and Efficacy in the 4T1 Mouse Tumor Model 6- or 7-week-old female Balb/c mice were injected with $0.1\times10^6$ 4T1 tumor cells into the mammary fat pad. Tumors were allowed to develop until tumor size reached 500 $mm^3$. Liposomal formulations (HSPC 0:8:2, PazPC and PGPC 3:5:2) containing fluorescent label DiI/indocyanine green were injected i.v. Liposomal formulations were corrected to equal fluorescence (1 nmole/mouse) before injections. Mice were sacrificed after 1 or 6 hours. Organs and tumors were isolated.

For efficacy analysis of AS1517499-loaded liposomes, $1\times10^5$ Luc-cells were injected into the mammary fat pad, and tumors were allowed to develop to a size of 100 $mm^3$. Thereupon, treatment with AS1517499-loaded liposomes (8 mg/kg, intravenous administrations, twice a week) was started. Before sacrifice, mice were injected with 2.5 mg of D-Luciferin (Perkin-Elmer, Waltham, MA) and were imaged after 15 minutes to detect bioluminescence signal using a Pearl Trilogy imager (LICOR).

Quantification of Organ and Tumor Accumulation

Approximately equal amounts of frozen tissue from tumors, livers and spleens were lysed using RIPA buffer (Thermo Fischer). Tissues were homogenized thoroughly. Fluorescence in lysates was determined using the Victor 3 fluorescent plate reader. Fluorescence was corrected for protein content, determined using BCA kit (Thermo Fisher).

Cellular Localization

Sections were cut from isolated organs and tumors and stained for macrophage marker F4/80 (Bio-rad) or CD206 (Santa Cruz) overnight. Secondary antibodies Rabbit anti Rat and Rabbit anti Goat (Dako) were used. Alexa 488 Donkey anti Rabbit (Thermo Fisher) antibodies were used for visualization. Sections were scanned using the Hamamatsu NanoZoomer Digital slide scanner 2.0HT (Hamamatsu Photonics, Bridgewater NJ).

Statistical Analysis

Data are presented as mean+standard error of the mean (SEM). All graphs were created and statistical analysis was performed using Graphpad Prism (Graphpad, La Jolla, CA) using two-sided unpaired student's T-test, unless otherwise specified. Statistical tests were performed with a minimum significance level of $p<0.05$.

Results

CyPC Liposomes Preparation and Characterization

Two different forms of carboxylated lipids (CyPCs) were selected and tested: PAzPC and PGPC (FIG. 1A). These lipids were incorporated into liposomes at different molar ratios. Size, polydispersity index (PDI) and zeta potential were determined, as shown in Table 1. The prepared liposomal preparations ranged from 80 (PGPC 2:6:2) to approximately 105-116 nm (other formulations) in mean size, with a small size distribution (FIG. 1C). To quantify the incorporated amount of carboxylated lipid into these liposomes, a uIPLC method using a corona CAD detector has been developed. Typical chromatograms showing lipid mixtures of liposome components are shown in FIG. 1B. Using this method, the total amounts and molar ratios of CyPC in the prepared liposomes was investigated (Table 2).It is found that the molar ratios for HSPC and PAzPC were comparable to the starting ratio, whereas the observed ratio PGPC-containing liposomes slightly deviated from the input ratio.

TABLE 2

Size, Polydispersity index (both measured in PBS) and zeta potential (in 0.1 mM KCl solution) of different compositions of liposomes. Molar ratios are shown between brackets. Results are shown from 2-5 different batches of liposomes, mean + SD.

| Formulations | Size (nm ± SD) | PDI (±SD) | Zeta potential (mV ± SD) |
|---|---|---|---|
| HSPC (0:8:2) | 115.9 ± 6.2 | 0.12 ± 0.05 | −22.6 ± 4.8 |
| PAzPC (2:6:2) | 107.9 ± 0.7 | 0.19 ± 0.06 | −25.1 ± 4.9 |
| PAzPC (3:5:2) | 105.9 ± 15.7 | 0.22 ± 0.04 | −27.8 ± 4.6 |
| PGPC (2:6:2) | 80.1 ± 0.9 | 0.20 ± 0.10 | −17.0 ± 6.0 |
| PGPC (3:5:2) | 113.5 ± 16.5 | 0.2 ± 0.08 | −21.1 ± 2.8 |

Stability of Liposomes

Stability of the prepared liposomes was investigated at 37° C. for up to 24 hours in culture medium. Results are shown in FIG. 1D. HSPC and PAzPC liposomes remained stable over the course of 24 hours, PGPC liposomes increased in size starting after 7 hours of incubation. To verify the fluorescent label DiI did not degrade or leak from the liposomal preparations, samples at 37° C. in culture medium for 24 hours (FIG. 1E) were dialyzed. Any loss of fluorescence was not detected, indicating the label remained inside the lipid bilayer of the liposomes during this time.

One batch of liposomes was tested in long term stability. The size of liposomes were checked after 3 weeks of storage in PBS at 4° C. and little change in size was found, and a slight increase in PDI (Table 3). These results indicate the liposomes remained stable during this time.

TABLE 3 uHPLC analysis of lipid content of CyPC-containing liposomes. Values are shown in mM, with theoretical amounts between brackets. The calculated molar ratio according to uHPLC analysis is shown in the last column.

| | CyPC (mM) | HSPC (mM) | Cholesterol (mM) | Molar ratio |
|---|---|---|---|---|
| HSPC (0:8:2) | — | 1.6 (2) | 0.4 (0.5) | 8:2 |
| PAzPC (2:6:2) | 0.4 (0.5) | 1.15 (1.5) | 0.5 (0.5) | 2:5.6:2.4 |
| PAzPC (3:5:2) | 0.6 (0.75) | 1.0 (1.25) | 0.4 (0.5) | 3:5:2 |
| PGPC (2:6:2) | 0.7 (0.5) | 1.5 (1.5) | 0.7 (0.5) | 2.4:5:2.4 |
| PGPC (3:5:2) | 0.4 (0.75) | 0.9 (1.25) | 0.4 (0.5) | 2.4:5.3:2.4 |

TABLE 4

Size and PDI of one batch of different CyPC-containing liposomal formulations, stored at 4° C. for 3 weeks. Mean ± SD.

| | Size (nm ± SD) Start | PDI (±SD) Start | Size (nm ± SD) 3 weeks | PDI (±SD) 3 weeks |
|---|---|---|---|---|
| HSPC (0:8:2) | 116.1 ± 3.36 | 0.06 ± 0.01 | 118.0 ± 0.36 | 0.12 ± 0.01 |
| PAzPC (3:5:2) | 83.34 ± 3.34 | 0.17 ± .003 | 87.23 ± 2.94 | 0.22 ± 0.01 |
| PGPC (3:5:2) | 96.79 ± 2.57 | 0.14 ± 1.5 | 91.9 ± 0.44 | 0.16 ± 0.03 |

Figure 2:
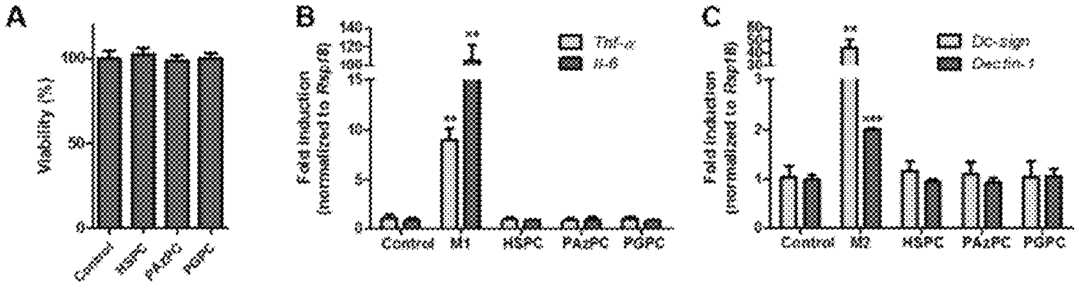
FIG. 2: Viability and gene expression of macrophages treated with CyPC-containing liposomes. (A) Viability of PMA-differentiated macrophages, treated with CyPC-containing liposomes (0:8:2 or 3:5:2 CyPC:HSPC:Cholesterol molar ratio at 50 μM) for 24 hours. (B and C) Gene expression data on M1 macrophage associated genes (Tnf-α, Il-6, B) and M2 macrophage associated genes (Dc-sign, Dectin-1, C) of PMA-differentiated macrophages, treated with CyPC-containing liposomes (50 μM) for 24 hours. All experiments n=3, mean+SEM, p<0.01, *p<0.001 vs control.

Effect of CyPC-Containing Liposomes on the Viability and Differentiation State of Macrophages In order to examine the effects of the prepared nanoparticles on macrophages, their toxicity and effect on differentiation on macrophages was first determined. In the PMA-activated macrophages, CyPC-containing liposomes were incubated for 24 hours. Results are shown in FIG. 2A. It was found that all tested formulations showed no effect on the macrophage viability. Next to toxicity, the effect of liposomes on macrophage differentiation was investigated using the same method. After 24-hour incubation, changes could not be detected in gene expression of M1 (Tumor necrosis factor α (Tnf-α) and Interleukin 6 (11-6)) and M2 (Dc-sign (Cd209) and Dectin-1 (Clec7a)) related genes, indicating that the liposomes did not differentiate the macrophages into either the M1 or the M2 phenotype.

Uptake of CyPC by Differentiated Macrophages

Figure 3:
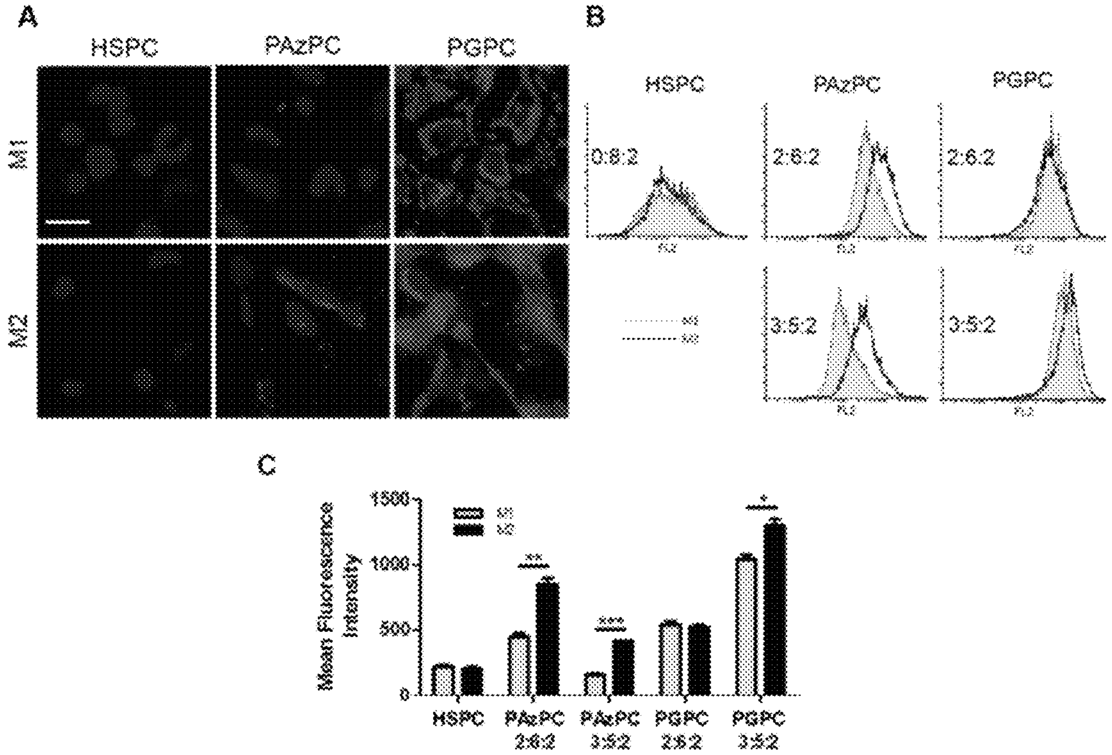
FIG. 3: Uptake of CyPC-containing liposomes by differentiated macrophages. (A) Representative fluorescent images of cellular uptake of CyPC-containing liposomes by differentiated M1 and M2 macrophages, incubated for 2 hours. Blue: DAPI, Red: CyPC-containing liposomes (3:5:2; CyPC:HSPC:Cholesterol molar ratio) labeled with DiI, bar=25 μm). (B) Representative flow cytometry histograms of M1 and M2 differentiated macrophages, incubated with CyPC-containing liposomes (different ratios) for 2 hours. (C) Quantification of flow cytometry data. All experiments n=3, mean+SEM, *p<0.05, p<0.01, *p<0.001 vs M1.

To evaluate the uptake of CyPC-containing liposomes by M1 and M2 differentiated macrophages, liposomes with CyPC:HSPC:Cholesterol molar ratio 3:5:2 were incubated with differentiated macrophages (FIG. 3A) and examined using fluorescent microscopic. HSPC liposomes were taken up in low and similar amounts and by both types of macrophages. A striking difference in uptake between M1 and M2 cells was seen using PAzPC-containing liposomes. Highest uptake was achieved using PGPC-containing liposomes, however, the difference between M1 and M2 cellular uptake was smaller. The cellular uptake was then quantified using flow cytometry and confirmed the observation that PAzPC were taken up much more by M2 compared to M1, while differences in case of PGPC were smaller, yet statistically significant (FIGS. 3B and 3C). Next to human cells, the specific uptake of PAzPC-containing liposomes was also confirmed in murine bone marrow derived macrophages (BMDM). BMDM were first differentiated into M1 and M2 phenotypes. Gene expression analysis confirmed differentiation. Upon incubation with liposomes, M2 differentiated cells showed significantly higher uptake of PAzPC-containing liposomes, compared to M1 cells.

Figure 4:
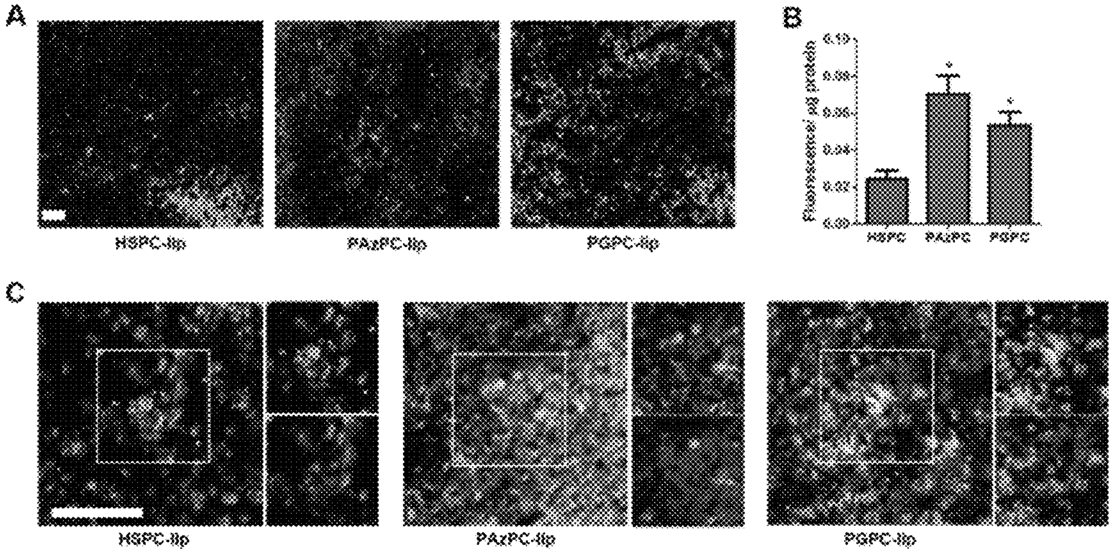
FIG. 4: Tumor distribution of liposomes in 4T1 tumor-bearing mice. (A) Representative images of liposome distribution (0:8:2 or 3:5:2 CyPC:HSPC:Cholesterol molar ratio) in tumor tissues, 1 hour after injection. Red: liposomes labeled with DiI, green: macrophage marker F4/80, blue: DAPI (B) Quantification of fluorescence in tumor homogenates. (C) Fluorescent images of macrophage-liposome co-localization within tumor tissues. Red: liposomes labeled with DiI, green: M2 macrophage marker CD206, blue: DAPI. Bar=50 μm. All experiments n=3, mean+SEM, *p<0.05 vs HSPC.

In Vivo Distribution and Uptake of CyPC-Containing Liposomes into Tumor Tissues and Organs To evaluate the effects of CyPC-containing liposomes on tissue distribution in vivo, mice were injected with 4T1 breast cancer tumor cells into the mammary fat pad. When tumors reached 500 $mm^3$, mice were injected with CyPC-containing liposomes via the tail vein and sacrificed after 1 hour. Tumors and organs were isolated. Upon examination of tumor tissues using the microscope, clear differences in tumor accumulation between normal and CyPC-containing liposomes could be seen (FIG. 4A). Both types of CyPC-containing liposomes showed increased tumor accumulation, compared to normal liposomes. This was confirmed by quantification of tumor fluorescence using tissue lysates (FIG. 4B). Co-localization of liposomes and TAMs (CD206, green) is shown in FIG. 4C. As can be seen, although all liposomes show some co-localization with TAMs, it was the most pronounced in PAzPC liposomes.

Figure 5:
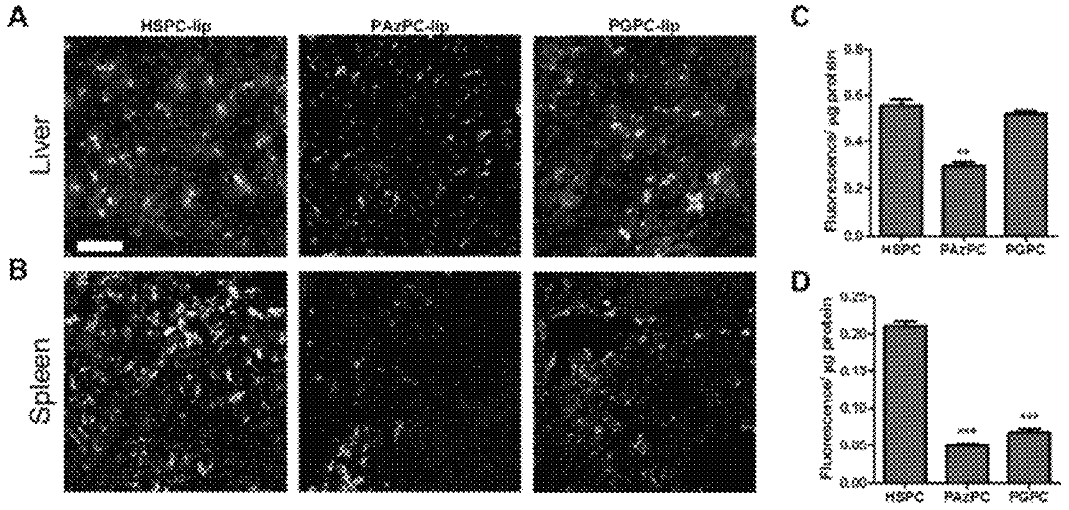
FIG. 5: Liver and spleen organ distribution of liposomes in 4T1 tumor-bearing mice. (A and B) Representative fluorescent images of liposome (0:8:2 or 3:5:2 CyPC:HSPC:Cholesterol molar ratio) distribution within the liver (A) and spleen (B), 1 hour after injection. Red: liposomes labeled with DiI, green: macrophage marker F4/80, blue: DAPI. Bar=50 μm (C and D) Quantification of organ fluorescence of tissue homogenates. All experiments n=3, mean+SEM, p<0.01, *p<0.001 vs HSPC.

Uptake of liposomes in other organs was also examined (FIG. 5). PAzPC-containing liposomes showed significantly less uptake in liver tissues, compared to normal and PGPC-containing liposomes. Furthermore, both PAzPC- and PGPC-containing liposomes accumulated significantly less in spleen tissues.

Mechanism of Specific M2 Uptake

Figure 6:
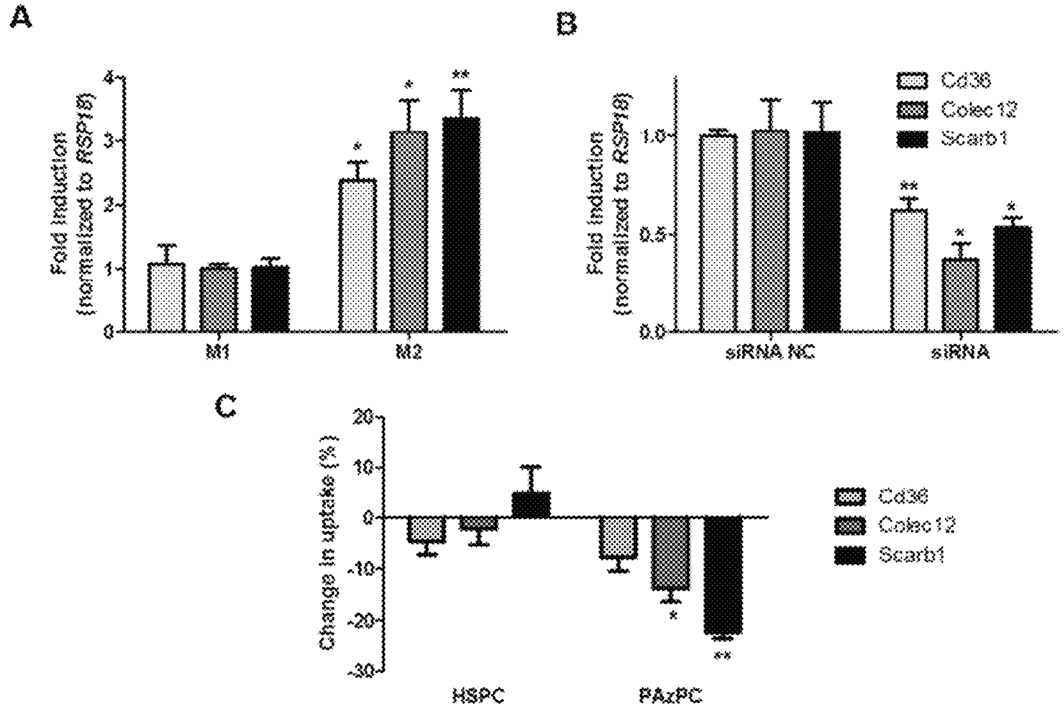
FIG. 6: Mechanism of action of specific uptake of CyPC-containing liposomes by M2 macrophages. (A) Gene expression data on M2 specific surface receptors Cd36, Colec12 and Scarb1. (B) Treatment with siRNA complexes reduces the gene expression of Cd36, Colec12 and Scarb1 in M2 differentiated macrophages. (C) Quantification of flow cytometry analysis of change in uptake after silencing of M2-specific surface receptors using HSPC liposomes (0:8:2 CyPC:HSPC:Cholesterol molar ratio) or PAzPC (3:5:2 CyPC:HSPC:Cholesterol molar ratio) after 2 hours of incubation. All experiments n=3-4, mean+SEM, *p<0.05, **p<0.01 vs M1 (A), siRNA NC (B) or HSPC (C).

In previous research, the differences in phagocytosis-related genes in M1 and M2 cells [7] was investigated. From this research, 3 different receptors were selected, involved in oxidized lipid uptake; cluster of differentiation 36 (CD36), scavenger receptor class B member 1 (Scarb1) and collectin subfamily member 12 (Colec12) and reconfirmed their upregulation in M2 cells (FIG. 6A). To study the role of these receptors in uptake, siRNA was used to silence these receptors in M2 differentiated macrophages (FIG. 6B) and subsequently investigated the uptake of normal and PAzPC-containing liposomes. It was found that silencing of the mentioned receptors did not affect HSPC liposome uptake (FIG. 6C). In contrast, PAzPC liposomes showed a significant reduction in the uptake upon silencing the investigated genes in the following order (Cd36<Colec12<Scarb1). These data indicate that amongst the investigated receptors, Colec12 and Scarb1, and Cd36, are responsible for the M2-specific uptake of CyPC-containing liposomes.

Preparation of AS1517499 Loaded PAzPC Liposomes

Figure 7:
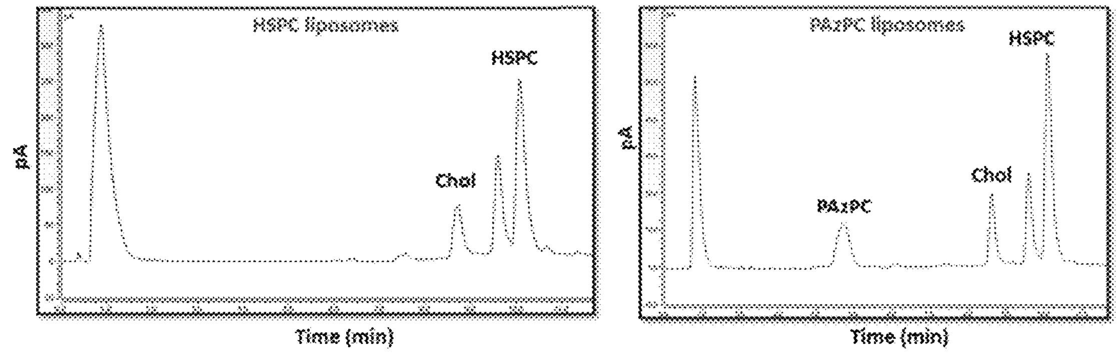
FIG. 7: Preparation and analysis of liposomes. The representative chromatogram of lipid mixtures analyzed using uHPLC separation with corona CAD.

Carboxylated lipids, which are the natural ligands for the phagocytosis receptors, were incorporated into liposomes. The well-characterized, stable carboxylated (PAzPC) was selected and tested in this study. These lipids were incorporated into liposomes at different molar ratios. Typical chromatograms showing lipid mixtures of liposomes components are shown in FIG. 7. The prepared liposomal preparations ranged from 90-120 nm in mean size, with small size distribution. To quantify the incorporated amount of drug into these liposomes, samples were measured at 261 and 306 nm using ND-1000 spectrophotometer. Size, polydispersity index and drug encapsulation were determined, as shown in Table 5.

TABLE 5

Size and PDI of one batch of different liposomal formulations.

| Formulations | Size (nm) | PDI | AS drug encapsulation |
|---|---|---|---|
| HSPC:Chol (8:2) | 103 | 0.12 | — |
| PAzPC:HSPC:Chol (3:5:2) | 96 | 0.18 | — |
| HSPC:Chol-AS (8:2) | 118 | 0.09 | 29% |
| PAzPC:HSPC:Chol-AS (3:5:2) | 115 | 0.15 | 46% |

Effect of AS-Loaded Liposomes on the 4T1 Breast Tumor Model

Figure 8:
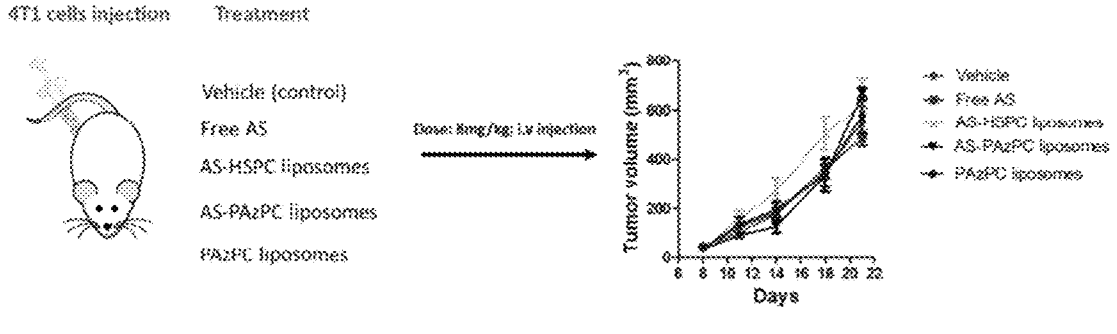
FIG. 8. In vivo effect of AS1517499 loaded liposomes treatment on tumor growth. Tumor volume of vehicle and AS treated animals (8 mg/ml, i.p, twice weekly) in days post tumor cell injection.

Mouse 4T1-Luc cells were injected orthotopic into the mammary fat pad of BalbC mice. The mice were randomly assigned into five groups: a) treated with PBS as the vehicle group, b) treated with free AS, c) treated with AS-HSPC liposomes, d) treated with AS-PAzPC liposomes, e) treated with empty PAzPC liposomes. Postma et al. showed treatment with free AS1517499 (20 mg/kg; i.p route) inhibited tumor volume significantly compared to the vehicle group and reduced premetastatic niche in liver (Binnemars-Postma et al. 2018 FASEB J. 32, 969-978, doi:10.1096/fj.201700629R). Since the loading of the AS1517499 was little in the liposomes, 8 mg/kg was injected, intravenous route, twice weekly. Surprisingly, there was no difference in tumor volume/weight in the AS alone group or AS-loaded liposome groups compared to the vehicle group (FIG. 8). Since the injection route and dose was different compared to the study by Postma et al., no difference was observed in tumor growth. Of note, it was found that the treatment had no effect on body weight, and there was no statistically significant difference between the weight of the organs (liver and lungs) among the five groups (data not shown).

Effect of AS-Loaded Liposomes on Liver and Lung Metastasis

Figure 9:
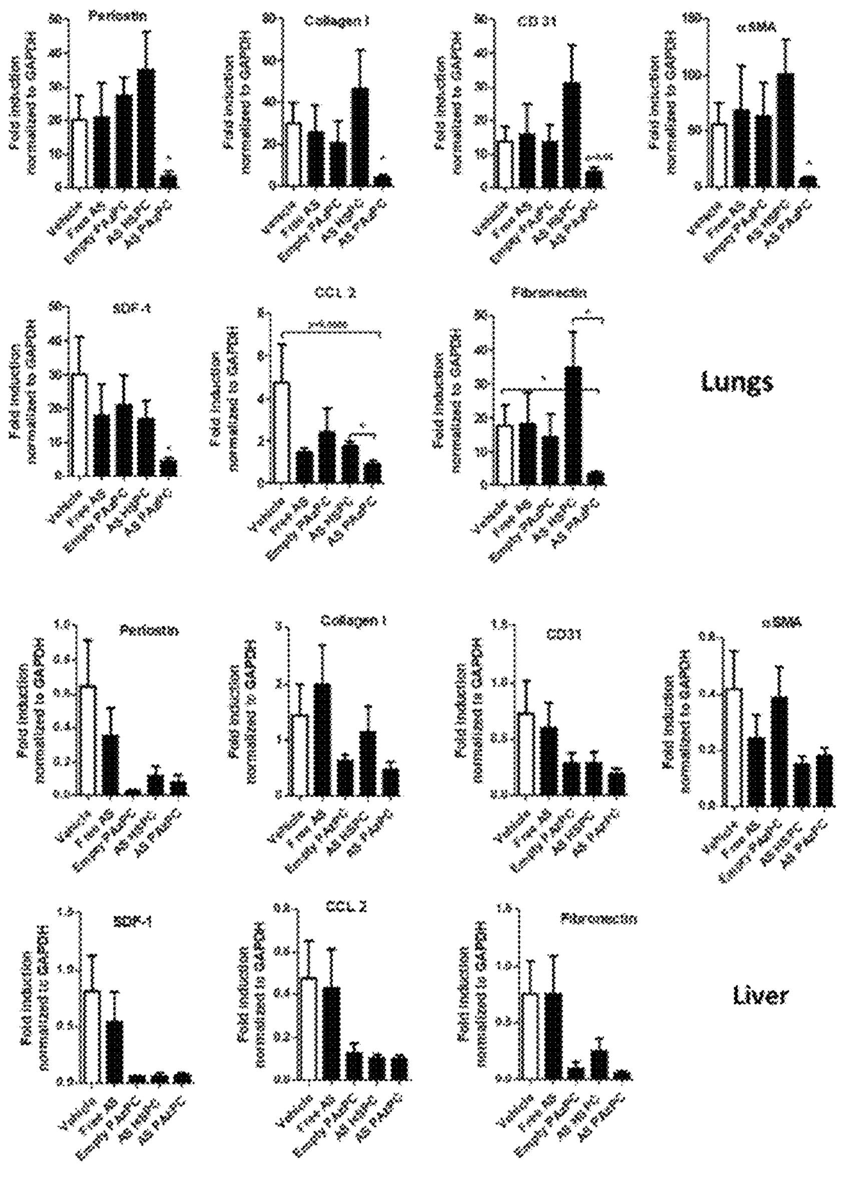
FIG. 9. In vivo effect of AS-loaded liposomes on metastasis. Quantitative real-time PCR results showing the macrophage and tumor progression markers measured in liver and lungs of tumor bearing animals treated and untreated with AS1517499-loaded liposomes. N=6 per group, data shown as mean+SEM *p<0.05.

TAMs display a number of pro-tumoral functions, including extracellular matrix remodeling, neoangiogenesis, suppression of adaptive immunity and facilitate tumor metastasis (Allavena et al. 2012 *Exp. Immunol.* 167, 195-205, doi:10.1111/j.1365-2249.2011.04515.x). Several studies summarized in a recent review by Peinado et al., have demonstrated that tumor cells secrete extracellular vesicles and growth factors at the primary site, which migrate to the metastatic site to harbor and nourish tumor cells (Peinado et al. 2017 *Nat. Rev. Cancer* 17, 302-317, doi:10.1038/ nrc.2017.6). As most of cancer related mortalities occur due to metastasis, the effect of AS-loaded liposomes on the pre-metastatic niche in the organs (liver and lungs) of the 4T1 breast tumor was examined using qPCR analysis (FIG. 9). In liver samples, it was found that CD31, collagen I, periostin, fibronectin was significantly reduced by AS-loaded PAzPC liposomes compared to the vehicle group. However, there was no statistically significant difference in the AS alone group. Similarly, in lungs samples, it was found that periostin, collagen I, CD31, acta2, SDF-1, CCL2, and fibronectin was significantly reduced by AS-loaded PAzPC liposomes compared to either vehicle or AS-loaded HSPC liposome groups. Interestingly in lung samples, therapeutic efficacy by empty PAzPC liposomes compared to the liver samples was not found.

In vivo Biodistribution of M2 Targeted Liposomes into Tumor Tissues and Organs

Figure 10:
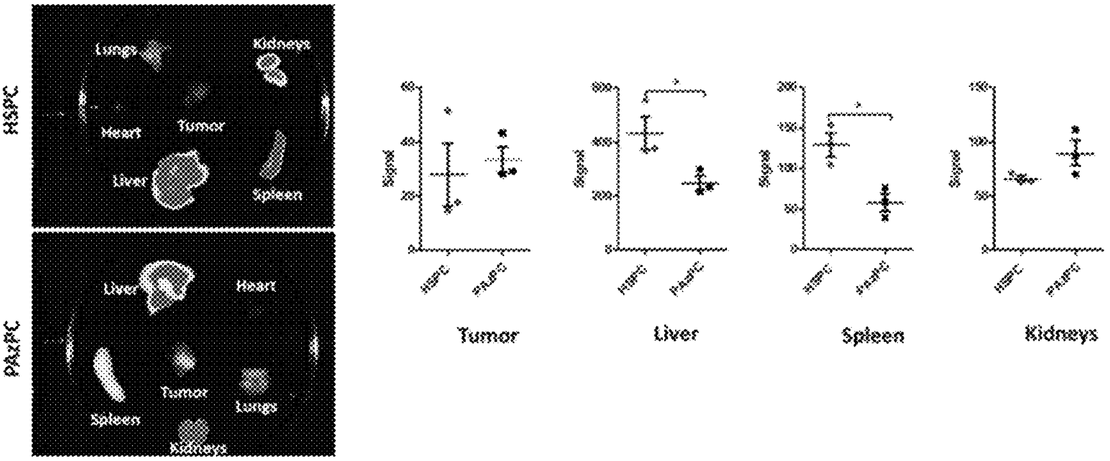
FIG. 10. Tumor distribution of liposomes loaded with ICG in 4T1 tumor bearing mice. The representative images of liposome distribution in tumor and different organs, 6 hours after injection. PAzPC liposomes showed increased tumor accumulation, compared to normal liposomes and other organs shows decreased PAzPC liposomal accumulation. N=3 per group, data shown as mean+SEM, *p<0.05.

To evaluate the effects of PAzPC liposomes on organ distribution in vivo, mice were injected with 4T1 breast tumor cells into the mammary fat pad. When tumors reached 200 $mm^3$, mice were injected with indocyanine-containing PAzPC or HSPC liposomes via the tail vein and sacrificed after 6 hours. Tumors and organs were isolated and imaged using Pearl Trilogy imager (LICOR). PAzPC liposomes showed increased tumor accumulation compared to the HSPC liposomes (FIG. 10). This was confirmed by the signal quantified using LICOR imager. In the liver and spleen, organs, which play a major role in the clearance of nanoparticles. PAzPC-containing liposomes showed a significant reduction in the liver and spleen compared to HSPC liposomes. This indicates HSPC liposomes are rapidly cleared from circulation, due to liver and spleen uptake, while PAzPC liposomes avoid this uptake. Greater tumor accumulation for these liposomes may therefore be achieved via higher availability of the liposomes and due to active uptake by TAM in tumor tissues.

Effect of MTP-PE on Murine RAW 264.7 Macrophages In Vitro

Figure 11:
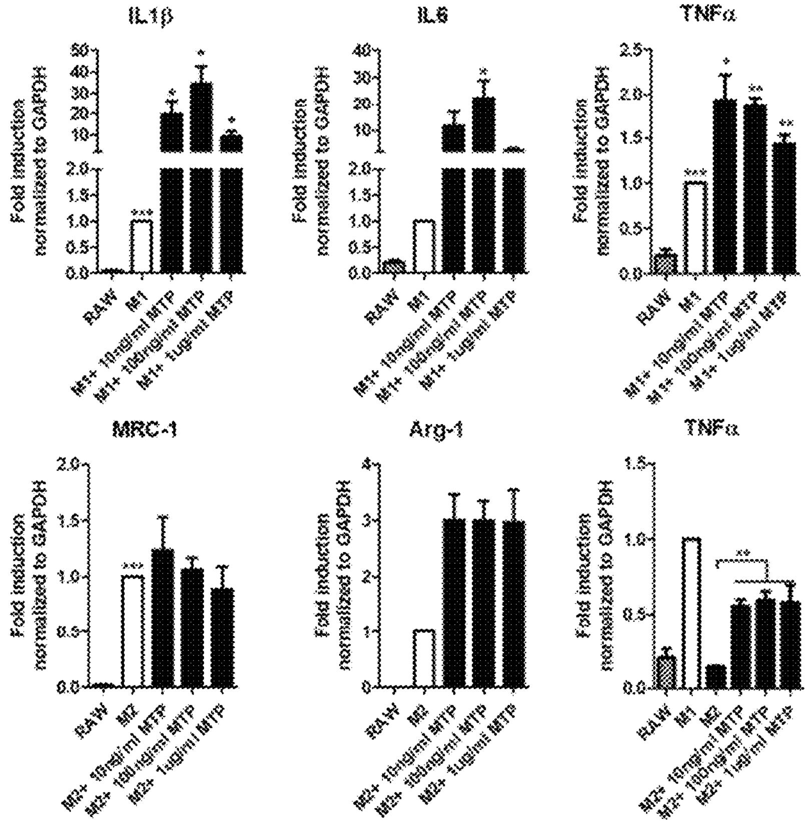
FIG. 11. In vitro effects of MTP-PE in differentiated RAW 264.7 macrophages. Quantitative gene expression analysis of macrophage differentiation with increasing concentrations of MTP-PE for M1 markers IL-1β, IL-6, TNFα and M2 markers for MRC-1 and ARG-1. Bars represent mean+SEM, n=3 *p<0.05, p<0.005, *p<0.001.

To study the effect of MTP-PE, murine macrophages RAW 264.7 were first differentiated with IFNγ and LPS for M1 and with IL-4 and IL-13 for M2 macrophages (TAM). Using qPCR, the differentiation of phenotypes was confirmed and the synergistic effect of MTP-PE was studied in the presence of cytokines (FIG. 11). Several studies have demonstrated that MTP-PE in the presence of IFNγ induces secretion of antitumor cytokines. Similarly, in the study it was found that IFNγ (in M1 differentiation) synergizes with MTP-PE (dose-dependent conc.) by increasing the cytokines (IL-1β, IL-6, TNFα) expression. In contrast, treatment of M2 macrophage with MTP-PE did not show any inhibition of M2 macrophage markers, but instead the increased TNFα expression in M2-type macrophages was found, which indicates the reprogramming of M2 macrophages toward M1 phenotype.

Effect of MTP-PE and INFγ on THP-1 Macrophages

Figure 12:
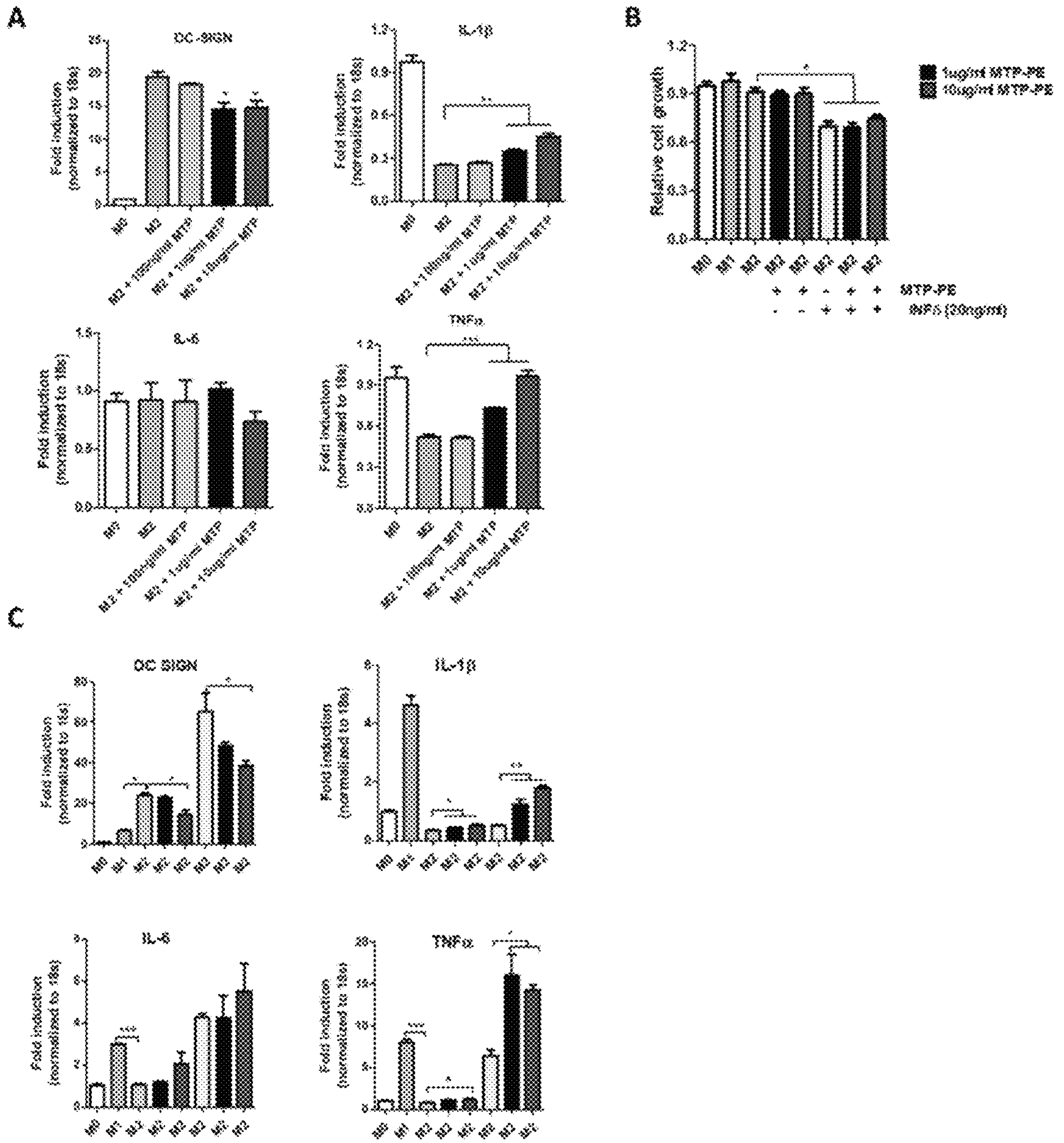
FIG. 12. In vitro effects of MTP-PE and IFNγ in differentiated THP-1 macrophages. qPCR analysis of macrophage differentiation with MTP-PE with or without IFNγ for M1 markers IL-1β, IL-6, TNFα and M2 markers for DC-SIGN. A) MTP-PE treatment inhibits M2 marker and activates tumoricidal properties by upregulating M1 markers. B) The cell growth was evaluated after 24-hour treatment of MTP-PE and IFNγ C) MTP-PE, in synergy with IFNγ activates tumoricidal properties by inducing more M1 markers. Bars represent mean+SEM, n=3 *p<0.05, p<0.005, *p<0.001.

Next, the effect of MTP-PE on differentiated human macrophages THP-1 was investigated. In the first experiment, it was found that treatment with MTP-PE (1 and 10 ug/ml) inhibited the differentiation of macrophages into the M2 type (TAMs), as shown with the reduced expression of DC-SIGN gene, a marker for M2 type (FIG. 12A). Consistent with RAW 264.7 macrophages data, treatment with MTP-PE in presence of M1 cytokines, increased the M1 type differentiation markers (data not shown). Interestingly, treatment with MTP-PE induced M1 cytokine markers (IL-1β and TNFα) in TAMs, which indicates the switch of M2 macrophages toward M1 phenotype (FIG. 12A). In the second experiment, IFNγ, a well-known inducer of M1 macrophage differentiation, was tested (Sica et al. 2012 *J. Clin. Invest.* 122, 787-795, doi:10.1172/JCI59643), and MTP-PE to understand the role of IFNγ potentiation effect on macrophage reprogramming. Results show that MTP-PE alone has no direct effect on the cell growth, but treatment of IFNγ (20 ng/ml) with or without MTP-PE reduced the cell growth significantly (FIG. 12B). Intriguingly, TAMs treated with IFNγ showed increased expression of DC-SIGN (M2 marker) but MTP-PE treatment reduced the expression of DC-SIGN. Furthermore, increased expression of M1 macrophage markers (IL-1β and TNFα) with co-treatment of IFNγ and MTP-PE was found. Altogether, these data suggest that MTP-PE and IFNγ support the plasticity of polarizing the M2 macrophages into M1 phenotype, but the mechanism for this potentiation is not known.

Preparation and Uptake of MTP-PE-Loaded Liposomes

Figure 13:
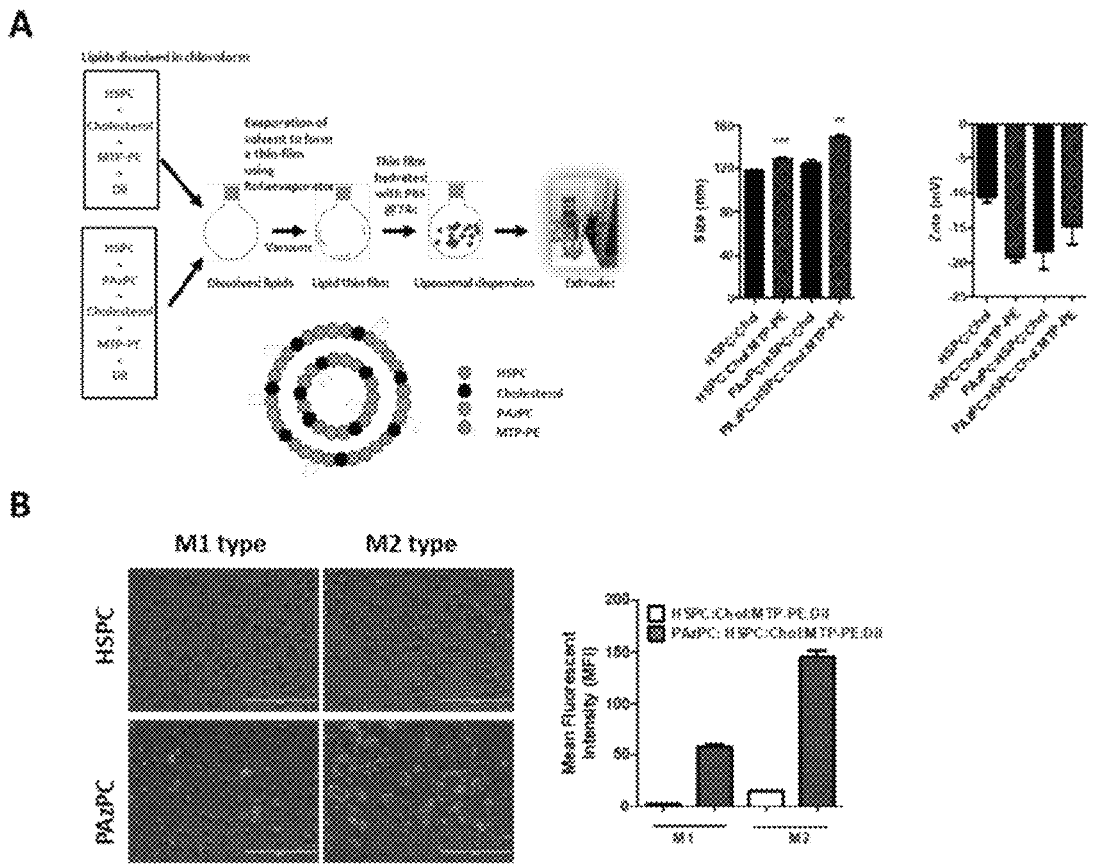
FIG. 13. Preparation of MTP-PE loaded liposomes. A) Representative scheme shows the preparation of MTP-PE loaded liposomes (PAzPC/HSPC) using rotaevaparotory method. The graphs show the liposomal size and zeta potential distribution. B) Uptake of liposomes by differentiated macrophages. The representative fluorescent images of cellular uptake of DiI loaded liposomes by differentiated M1 and M2 macrophages, incubated for 2 hours. Quantification of flow cytometry data, all experiments n=3, mean+SEM.

HSPC lipid with or without PAzPC lipid in the presence of MTP-PE lipid were incorporated into liposomes with DiI at different molar ratios. Size, and zeta potential were determined, as shown in Table 6. The prepared liposomal preparations ranged from 120-150 nm in mean size, with small size distribution (FIG. 13A). Of note, to quantify the incorporated amount of MTP-PE into these liposomes was not measured, but a great difference in mean size was observed with or without MTP-PE. To evaluate the uptake of MTP-PE containing liposomes by M1 and M2 differentiated macrophages. The liposomes loaded MTP-PE containing liposomes (HSPC/PAzPC) were incubated with differentiated macrophages and examined using fluorescent microscopy and flow cytometry analyses. HSPC liposomes were taken up low by both types of macrophages. A striking difference in uptake between M1 and M2 cells was seen using PAzPC liposomes (FIG. 13B). The cellular uptake was then quantified using flow cytometry and confirmed the observation that PAzPC were taken up much more by M2 compared to M1.

TABLE 6

Size (measured in PBS), zeta potential (in 10 mM Kcl solution) of different compositions of liposomes. Molar ratios are shown in between brackets.

| Formulations (Molar ratios) | Size (nm ± SD) | Zeta potential (mV ± SD) |
|---|---|---|
| HSPC:PAzPC:Chol:DiI:MTP-PE (7.8:0:2:0.1:0.2) | 128.3 ± 1.15 | −19 ± 1 |
| HSPC:PAzPC:Chol:DiI:MTP-PE (4.8:3:2:0.1:0.2) | 149 ± 2.35 | −15 ± 4.35 |

Re-Polarization of TAMs Using Co-Delivery of MTP-PE and IFNγ

Figure 14:
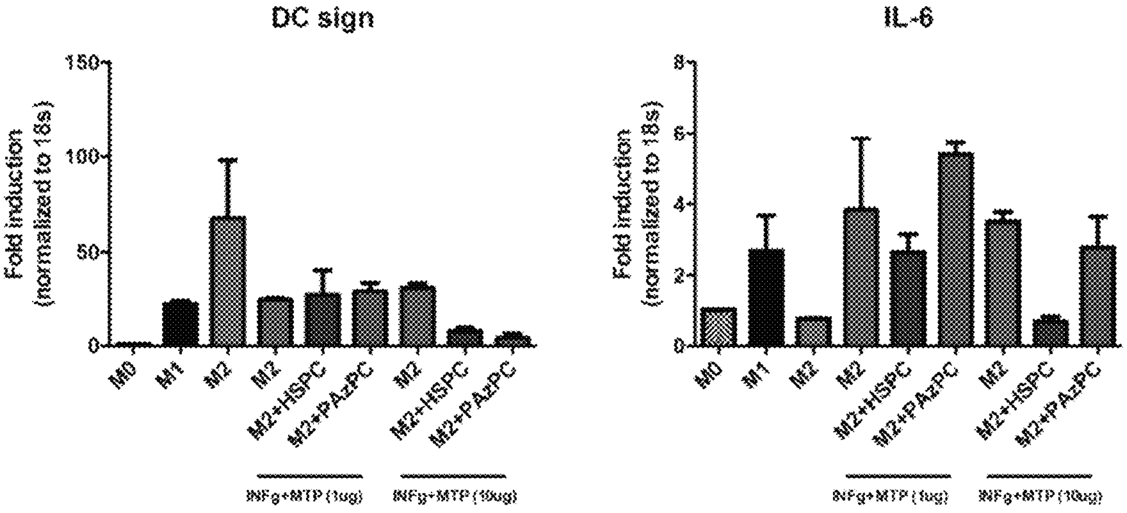
FIG. 14. Re-polarization of M2 macrophages into M1 type. Gene expression levels of M2 marker DC sign and M1 marker IL-6 showing re-polarization of M2 into M1 after incubation with MTP-PE/IFNγ encapsulating HSPC-liposomes and PAzPC liposomes.

MTP-PE was co-encapsulated (into lipid bilayer) and IFNγ (into aqueous layer) into PAzPC liposomes and studied the effect on the repolarization of already M2 differentiated macrophages. THP-1 monocytes were first differentiated into M2 macrophages and then treated with MTP-PE/IFNγ-PAzPC liposomes and controls and the gene expression key gene markers for M2 (DC sign) and M1 (IL-6) (FIG. 14) were examined. It was found that the targeted liposomes repolarized M2 into M1, as can be seen with reduced expression levels of DC sign marker and induced expression levels of IL-6. These data show that both a bioactive peptide-lipid, i.e., MTP-PE and a cytokine (IFNγ) can be delivered using the targeted liposomes and re-polarize TAMs into anti-tumoral M1 macrophages.

Discussion

Macrophage targeting and depletion has been described extensively in literature [5, 18]. Additionally, macrophage polarization in disease conditions is a growing field of research [19-22]. Moreover, the functions of differentiated macrophages are becoming more and more clear. As M1 macrophages may be beneficial in cancer immunity, the specific targeting of TAM subpopulation in the treatment of cancer may be an effective way to treat these macrophages [5, 23, 24]. Tumor-promoting macrophages (i.e., M2 macrophages/TAMs) were specifically targeted. Without being bound, likely through M2-induced surface receptors CD36, Collectin subfamily member 12 and Scavenger receptor class B member 1. Carboxylated lipids, which are the natural ligands for these receptors [10, 25-27], were incorporated into small unilamellar liposomes. The carboxylated lipids PAzPC and PGPC were selected and incorporated them at several ratios into liposomes composed of the carrier lipid HSPC and cholesterol.

Size stability was investigated over a period of 24 hours at 37° C. in culture medium, since these liposomes were not pegylated they are expected to circulate only for a few hours. During this period of time, HSPC and PAzPC liposomes remained stable while PGPC-containing liposomes increased in size after 7 hours of incubation, indicating these liposomes were less stable (FIG. 1C). The shorter oxidatively truncated tail of PGPC can flip to the outside of the lipid bilayer, whereas the somewhat longer tail of PAzPC is able to reside in the bilayer as well [9, 28]. This result in a more stable liposome. At 4° C., these formulations remained stable for up to 3 weeks with no change in their size (table 3). To rule out the possibility of leakage or transfer of the fluorescent dye out of the bilayer, which might cause false positive results during uptake studies, the retention of the dye in the lipid bilayer was investigated under similar conditions as in vitro experiments. Although there was an increase in size, no leakage of the dye was seen indicating that the dye was well retained due to its high lipophilic nature.

Recent reports have shown that liposomes or lipids may modulate the macrophage phenotype [11-15]. The application of pegylated liposomes in a murine cancer model promoted tumor growth and angiogenesis, while suppressing the anti-tumor immune response. Further investigation showed a decrease in Interferon-γ secreting (associated with M1) macrophages [14]. On the other hand, several studies have shown specifically oxidized lipids to induce inflammatory gene expression, most likely due to the interaction with Toll-like receptors (TLRs) [11-13, 15] or via transcription factor Nrf2 mediated gene expression [29]. As the aim of the study is to design a targeting strategy for the treatment of TAM, thereby reducing their tumor-promoting properties, the effect of the carriers on macrophage differentiation was investigated. The gene expression profiles of liposome-treated macrophages for well-known genes associated with M1 (Tnf-α and Il-6) and M2 (Dc-sign and Dectin-1) macrophage differentiation [7, 30-32] was analyzed. Macrophages were treated with M1 inducing (Lipopolysaccharide (LPS) and Interferon γ (IFN-γ)) and M2 inducing (IL-4 and IL-13) cytokines to provide positive controls. As can be seen in FIGS. 2B and 2C, treatment of macrophages with the liposomal preparations did not affect macrophage differentiation. Furthermore, no effect on cell viability was observed, suggesting these liposomes are not toxic and do not alter their phenotype. Based on these results, these liposomes may be applied for the targeting of TAM, without inducing cell death or macrophage differentiation.

Using fluorescent microscopy and flow cytometry, the differences between the liposomal uptake by M1 and M2 macrophages both microscopically and quantitatively (FIG. 2) were delineated. The most striking difference in M1 and M2 was seen using PAzPC liposomes at 3:5:2 molar ratio at which the liposomes became more specific to M2. The mechanism for the higher specificity of PAzPC for M2-like cells is not known. Tumor accumulation and organ distribution of both types of carboxylated lipid liposomes were tested in the 4T1 murine breast cancer model. Most interestingly, using carboxylated-lipid containing liposomes, 2-(PGPC) to 3-fold (PAzPC) increase in tumor fluorescence was found. Most importantly, the co-localization of PAzPC-containing liposomes with M2 macrophages (CD206 positive, FIG. 4C) was able to be shown. In HSPC and PGPC-containing liposomes the co-localization of liposomes and M2 macrophages was not as pronounced. In the liver and spleen, organs, which play a major role in the clearance of nanoparticles [33], PAzPC-containing liposomes showed an almost 2-fold reduction in uptake in the liver (FIG. 5C), while both CyPC-containing liposomes showed a huge reduction (3- and 4-fold for PGPC and PAzPC, respectively) in uptake by the spleen (FIG. 5D). As tissue macrophages have varying phenotypes [34], these macrophages were stained using the general macrophage marker F4/80. Liposomes and macrophage (F4/80 positive) co-localization seemed to be absent in livers for PAzPC-containing liposomes and in the spleen for both types of CyPC-containing liposomes. HSPC-containing liposomes are mostly clustered around macrophages in both organs. This indicates HSPC liposomes are rapidly cleared from circulation, due to liver and spleen uptake, while CyPC-containing liposomes avoid this uptake. Greater tumor accumulation for these liposomes may therefore be achieved via higher availability of the liposomes and due to active uptake by TAM in tumor tissues.

Due to the superior effects PAzPC-containing liposomes have shown in M2-macrophage specificity, tumor accumulation and organ distribution, these liposomes were chosen at a molar ratio of 3:5:2 to continue investigating the mechanism of action causing this specificity. In previous studies, differences in phagocytic receptors in M1 and M2 differentiated cells [7] were investigated. In this study, a number of up-regulated phagocytosis receptors in M2 differentiated cells were found. Of those receptors, the ones that are involved in oxidized lipid recognition and uptake were selected.

CD36 is a member of the scavenger receptor class B family [8, 35]. It has been shown to play a role in accumulation of cholesterol in atherosclerotic plaques, via uptake of oxidized lipoproteins [36, 37]. Furthermore, oxidized phosphatidylserine (OxPS), expressed by apoptotic cells, is recognized by CD36, resulting in recognition and engulfment of apoptotic cells [38]. Other types of oxidized lipids, including PAzPC and PGPC have been identified to interact with CD36 as well [10].

Of the same class as CD36 is Scarb1 [8]. Its major function is the selective uptake of cholesteryl esters from high density lipoprotein (HDL) and the initial steps of reverse cholesterol transport [39, 40]. Moreover, Scarb1 binds oxidized low density lipoproteins (OxLDL) with high affinity. Since this binding is inhibited via competition of free oxidized lipoproteins from LDL and E06, a selective antibody against oxidized phospholipids [41], this receptor is thought to play an important role in the binding of OxLDL by macrophages, mainly through the presence of oxidized phospholipids [25].

Colec12 is a member of the scavenger class A family [8]. This cell surface glycoprotein plays a role in host defense, due to its carbohydrate recognizing domain (CRD) [42]. Moreover, Ohtani et al. have shown this receptor to recognize, bind and internalize oxLDL [27].

Using gene expression analysis on differentiated M1 and M2 macrophages, these receptors were confirmed to be up-regulated in the M2 macrophage phenotype (FIG. 6A). To study the role of these receptors in the specific uptake of carboxylated-lipid containing liposomes by M2 macrophages, the genes for these receptors were selectively silenced. Using siRNA complexes, gene expression profiles were reduced significantly (FIG. 6B). Subsequently, the effect of this silencing on the uptake of normal and PazPC-containing liposomes was examined. Surprisingly, when using normal liposomes, silencing of the M2 specific uptake receptors did not affect liposome uptake at all (FIG. 6C), suggesting these receptors do not play a role in the recognition and internalization of HSPC liposomes by M2 macrophages. However, when using PAzPC-containing liposomes, the liposomal uptake was reduced in Colec12 and Scarb1-silenced cells. Cd36-silenced cells showed a small non-significant reduction in uptake (FIG. 6C). This suggests that Colec12 and Scarb1 play a major role in the recognition and uptake of PAzPC-containing liposomes by M2 macrophages.

It has been shown that the liposomes described herein can be employed in the specific targeting of TAM (i.e. M2 macrophages). As the detrimental role of TAM in the progression of cancer is becoming more and more clear [22], the specific targeting and treatment of these immune cells has become an active topic of investigation [5]. Recently, several compounds have been shown to inhibit TAM polarization, thereby reducing tumor growth and metastasis [43-46]. Liposomes are versatile, biodegradable and generally well-tolerated [47-49]. Carboxylated lipids are well-defined lipid molecules and can therefore be applied for the development of clinical products. Moreover, carboxylated lipids have been tested clinically [50], which may facilitate their clinical application for liposomal delivery. Therefore, the combination of liposomes and carboxylated lipids as a nanocarrier represents a very suitable candidate for drug encapsulation and delivery in a clinical setting.

It has been demonstrated that the stat6 inhibitor AS1517499 could be successfully encapsulated into TAM targeted PAzPC-liposomes, which inhibited metastatic niche formation in lungs in 4T1 breast tumor model. Furthermore, it is found that MTP-PE transforms macrophages into M1 type, anti-tumoral macrophage. Interestingly, incorporation of MTP-PE into PAzPC-liposomes was successfully performed and led to the specific uptake by M2 macrophages. These data indicate that using the TAM-targeted liposomes MTP-PE and IFNγ can be delivered to TAMs and potentially used for re-polarization into M1 macrophages.

CITED ART

1. Hanahan, D. and R. A. Weinberg, Hallmarks of cancer: the next generation. Cell, 2011. 144(5): p. 646-74.
2. Schooley, A. M., et al., beta 1 integrin is required for anchorage-independent growth and invasion of tumor cells in a context dependent manner. Cancer Letters, 2012. 316(2): p. 157-167.
3. Lander, A. D., et al., What does the concept of the stem cell niche really mean today? Bmc Biology, 2012. 10.
4. Valastyan, S. and R. A. Weinberg, Tumor Metastasis: Molecular Insights and Evolving Paradigms. Cell, 2011. 147(2): p. 275-292.
5. Binnemars-Postma, K., G. Storm, and J. Prakash, Nanomedicine Strategies to Target Tumor-Associated Macrophages. Int. J. Mol. Sci., 2017. 18(5).
6. Boullier, A., et al., Phosphocholine as a pattern recognition ligand for CD36. Journal of lipid research, 2005. 46(5): p. 969-76.
7. Binnemars-Postma, K. A., et al., Differential uptake of nanoparticles by human M1 and M2 polarized macrophages: protein corona as a critical determinant. Nanomedicine (Lond), 2016. 11(22): p. 2889-2902.
8. Murphy, J. E., et al., Biochemistry and cell biology of mammalian scavenger receptors. Atherosclerosis, 2005. 182(1): p. 1-15.
9. Beranova, L., et al., Oxidation changes physical properties of phospholipid bilayers: fluorescence spectroscopy and molecular simulations. Langmuir, 2010. 26(9): p. 6140-4.
10. Serbulea, V., D. DeWeese, and N. Leitinger, The effect of oxidized phospholipids on phenotypic polarization and function of macrophages. Free Radic. Biol. Med., 2017. 111: p. 156-168.
11. Cruz, D., et al., Host-derived oxidized phospholipids and HDL regulate innate immunity in human leprosy. J. Clin. Invest., 2008. 118(8): p. 2917-28.
12. Imai, Y., et al., Identification of oxidative stress and Toll-like receptor 4 signaling as a key pathway of acute lung injury. Cell, 2008. 133(2): p. 235-49.
13. Oskolkova, O. V., et al., Oxidized phospholipids are more potent antagonists of lipopolysaccharide than inducers of inflammation. J. Immunol., 2010. 185(12): p. 7706-12.
14. Sabnani, M. K., et al., Liposome promotion of tumor growth is associated with angiogenesis and inhibition of antitumor immune responses. Nanomedicine, 2015. 11(2): p. 259-62.
15. Walton, K. A., et al., Receptors involved in the oxidized 1-palmitoyl-2-arachidonoyl-sn-glycero-3-phosphoryl-cholinemediated synthesis of interleukin-8. A role for Toll-like receptor 4 and a glycosylphosphatidylinositol-anchored protein. J. Biol. Chem., 2003. 278(32): p. 9661-6.
16. Stemmer, U., et al., Toxicity of oxidized phospholipids in cultured macrophages. Lipids Health Dis., 2012. 11: p. 110.
17. Batzri, S. and E. D. Korn, Single bilayer liposomes prepared without sonication. Biochim. Biophys. Acta, 1973. 298(4): p. 1015-9.
18. Tang, X., et al., Anti-tumour Strategies Aiming to Target Tumour-associated Macrophages. Immunology, 2012.
19. Beljaars, L., et al., Hepatic Localization of Macrophage Phenotypes during Fibrogenesis and Resolution of Fibrosis in Mice and Humans. Front Immunol., 2014. 5: p. 430.
20. Sica, A., et al., Tumour-associated macrophages are a distinct M2 polarised population promoting tumour progression: potential targets of anti-cancer therapy. Eur. J. Cancer, 2006. 42(6): p. 717-27.
21. Colin, S., G. Chinetti-Gbaguidi, and B. Staels, Macrophage phenotypes in atherosclerosis. Immunol. Rev., 2014. 262(1): p. 153-66.
22. Mantovani, A., et al., Tumour-associated macrophages as treatment targets in oncology. Nat. Rev. Clin. Oncol., 2017. 14(7): p. 399-416.
23. Allavena, P. and A. Mantovani, Immunology in the clinic review series; focus on cancer: tumour-associated macrophages: undisputed stars of the inflammatory tumour microenvironment. Clin. Exp. Immunol., 2012. 167(2): p. 195-205.
24. Biswas, S. K. and A. Mantovani, Macrophage plasticity and interaction with lymphocyte subsets: cancer as a paradigm. Nat. Immunol., 2010. 11(10): p. 889-96.
25. Gillotte-Taylor, K., et al., Scavenger receptor class B type I as a receptor for oxidized low density lipoprotein. J. Lipid Res., 2001. 42(9): p. 1474-82.
26. Nelms, K., et al., The IL-4 receptor: signaling mechanisms and biologic functions. Annu. Rev. Immunol., 1999. 17: p. 701-38.
27. Ohtani, K., et al., The membrane-type collectin CL-P1 is a scavenger receptor on vascular endothelial cells. J. Biol. Chem, 2001. 276(47): p. 44222-8.
28. Amirkavei, M. and P. K. Kinnunen, Interactions and dynamics of two extended conformation adapting phosphatidylcholines in model biomembranes. Biochim. Biophys. Acta, 2016. 1858(2): p. 264-73.
29. Kadl, A., et al., Identification of a novel macrophage phenotype that develops in response to atherogenic phospholipids via Nrf2. Circ. Res., 2010. 107(6): p. 737-46.
30. Martinez, F. O., et al., Transcriptional profiling of the human monocyte-to-macrophage differentiation and polarization: new molecules and patterns of gene expression. Journal of Immunology, 2006. 177(10): p. 7303-11.
31. Relloso, M., et al., DC-SIGN (CD209) expression is IL-4 dependent and is negatively regulated by IFN, TGF-beta, and anti-inflammatory agents. Journal of Immunology, 2002. 168(6): p. 2634-43.
32. Willment, J. A., et al., The human beta-glucan receptor is widely expressed and functionally equivalent to murine Dectin-1 on primary cells. European Journal of Immunology, 2005. 35(5): p. 1539-47.
33. Alexis, F., et al., Factors affecting the clearance and biodistribution of polymeric nanoparticles. Mol. Pharm., 2008. 5(4): p. 505-15.
34. Haldar, M. and K. M. Murphy, Origin, development, and homeostasis of tissue-resident macrophages. Immunol. Rev., 2014. 262(1): p. 25-35.
35. Suzuki, H., et al., A role for macrophage scavenger receptors in atherosclerosis and susceptibility to infection. Nature, 1997. 386(6622): p. 292-6.
36. Endemann, G., et al., CD36 is a receptor for oxidized low density lipoprotein. J. Biol. Chem., 1993. 268(16): p. 11811-6.
37. Febbraio, M., et al., Targeted disruption of the class B scavenger receptor CD36 protects against atherosclerotic lesion development in mice. J. Clin. Invest., 2000. 105(8): p. 1049-56.
38. Greenberg, M. E., et al., Oxidized phosphatidylserine-CD36 interactions play an essential role in macrophage-dependent phagocytosis of apoptotic cells. J. Exp. Med., 2006. 203(12): p. 2613-25.
39. Acton, S., et al., Identification of scavenger receptor SR-BI as a high density lipoprotein receptor. Science, 1996. 271(5248): p. 518-20.
40. Ji, Y., et al., Scavenger receptor BI promotes high density lipoprotein-mediated cellular cholesterol efflux. J. Biol. Chem, 1997. 272(34): p. 20982-5.
41. Horkko, S., et al., Monoclonal autoantibodies specific for oxidized phospholipids or oxidized phospholipid-protein adducts inhibit macrophage uptake of oxidized low-density lipoproteins. J. Clin. Invest., 1999. 103(1): p. 117-28.
42. Nakamura, K., et al., Molecular cloning and functional characterization of a human scavenger receptor with C-type lectin (SRCL), a novel member of a scavenger receptor family. Biochem. Biophys. Res. Commun., 2001. 280(4): p. 1028-35.
43. Xue, N., et al., Chlorogenic acid inhibits glioblastoma growth through repolarizating macrophage from M2 to M1 phenotype. Sci. Rep., 2017. 7: p. 39011.
44. Jia, X., et al., Emodin suppresses pulmonary metastasis of breast cancer accompanied with decreased macrophage recruitment and M2 polarization in the lungs. Breast Cancer Res. Treat., 2014. 148(2): p. 291-302.
45. Pyonteck, S. M., et al., CSF-1R inhibition alters macrophage polarization and blocks glioma progression. Nat. Med., 2013. 19(10): p. 1264-72.
46. Binnemars-Postma, K., et al., Targeting the Stat6 pathway in tumor-associated macrophages reduces tumor growth and metastatic niche formation in breast cancer. FASEB Journal, 2018: 32(2):969-978.
47. Elizondo, E., et al., Liposomes and other vesicular systems: structural characteristics, methods of preparation, and use in nanomedicine. Prog. Mol. Biol. Transl. Sci., 2011. 104: p. 1-
48. Sercombe, L., et al., Advances and Challenges of Liposome Assisted Drug Delivery. Front Pharmacol., 2015. 6: p. 286.
49. Eloy, J. O., et al., Liposomes as carriers of hydrophilic small molecule drugs: strategies to enhance encapsulation and delivery. Colloids Surf. B. Biointerfaces., 2014. 123: p. 345-63.
50. Feige, E., et al., Modified phospholipids as anti-inflammatory compounds. Current opinion in lipidology, 2010. 21(6): p. 525-9.

The invention claimed is:

1. A method of preferentially providing tumor-associated M2 macrophages with a drug comprised in a liposome so as to treat a subject having cancer, the method comprising:

administering to the subject a composition comprising a liposome, wherein the liposome comprises:

a first phospholipid comprising a $C_{14}$-$C_{19}$:0 fatty acid and a $C_3$-$C_{15}$:0 fatty acid with a C-terminal carboxyl or a carboxaldehyde group, wherein the first phospholipid comprises 1-palmitoyl-2-azelaoyl-sn-glycero-3-phosphocholine (PAzPC);

a second phospholipid comprising two $C_{14}$-$C_{19}$:0 fatty acids; and a sterol.

2. The method according to claim 1, wherein the liposome further comprises a label.

3. The method according to claim 1, wherein the second phospholipid is a phosphatidylcholine selected from the group consisting of dipalmitoylphosphatidylcholine (DPPC), distearoylphosphatidylcholine (DSPC), a hydrogenated soybean phosphatidylcholine (HSPC), and a combination of any thereof.

4. The method according to claim 1, wherein the sterol is cholesterol.

5. The method according to claim 1, wherein the first phospholipid, the second phospholipid, and sterol are present in a molar ratio of, respectively, 0.5-8:1.5-24:0.5-8.

6. The method according to claim 1, wherein the second phospholipid comprises hydrogenated soybean phosphatidylcholine (HSPC), and the sterol is cholesterol.

7. The method according to claim 6, wherein the PAzPC, HSPC, and cholesterol are, respectively, in a molar ratio selected from the group consisting of 2-3:5-6:2-3, 2:6:2, and

3:5:2.

8. The method according to claim 1, wherein the drug is selected from the group consisting of a protein, a nucleic acid encoding a protein, an mRNA, an oligonucleotide, an antisense oligonucleotide, an siRNA, a miRNA, a splice modulating oligonucleotide, a gapmer, an lnRNA and combinations thereof.

9. The method according to claim 8, wherein the drug is a hydrophobic drug and the liposome further comprises a cyclodextrin.

* * * * *